US008409729B2

United States Patent
Zeng et al.

(10) Patent No.: US 8,409,729 B2
(45) Date of Patent: Apr. 2, 2013

(54) HOST MATERIALS FOR PHOSPHORESCENT OLEDS

(75) Inventors: Lichang Zeng, Ewing, NJ (US); Alexey B. Dyatkin, Ewing, NJ (US); Gregg Kottas, Ewing, NJ (US); Chuanjun Xia, Ewing, NJ (US); David Z. Li, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 13/193,173

(22) Filed: Jul. 28, 2011

(65) Prior Publication Data

US 2013/0026909 A1 Jan. 31, 2013

(51) Int. Cl.
*H01L 51/54* (2006.01)

(52) U.S. Cl. ............ 428/690; 428/917; 546/18; 546/79; 546/81; 546/101; 257/40; 257/E51.05; 257/E51.026; 257/E51.032; 313/504; 313/505; 313/506; 548/440

(58) Field of Classification Search ............ 546/18, 546/79, 81, 101; 428/690, 917; 257/40, 257/E51.05, E51.026, E51.032; 313/504, 313/505, 506; 548/440
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |

(Continued)

FOREIGN PATENT DOCUMENTS

| | | |
|---|---|---|
| CN | 101863914 | 10/2010 |
| EP | 0650955 | 5/1995 |

(Continued)

OTHER PUBLICATIONS

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

(Continued)

*Primary Examiner* — Jennifer Chriss
*Assistant Examiner* — Gregory Clark
(74) *Attorney, Agent, or Firm* — Kilpatrick Townsend & Stockton LLP

(57) ABSTRACT

Novel aryl silicon and aryl germanium host materials are described. These compounds improve OLED device performance when used as hosts in the emissive layer of the OLED.

18 Claims, 4 Drawing Sheets

U.S. PATENT DOCUMENTS

| | | | |
|---|---|---|---|
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0064238 | A1 | 3/2005 | Lee et al. |
| 2005/0112407 | A1 | 5/2005 | Ogasawara et al. |
| 2005/0214572 | A1 | 9/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2009/0236975 | A1 | 9/2009 | Ito |
| 2012/0012821 | A1* | 1/2012 | Langer et al. ............ 257/40 |

FOREIGN PATENT DOCUMENTS

| | | |
|---|---|---|
| EP | 1725079 | 11/2006 |
| EP | 2034538 | 3/2009 |
| EP | 2090637 | 8/2009 |
| JP | 200511610 | 1/2005 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2008056746 | 5/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2010079051 | 7/2010 |
| WO | WO 2010126234 | 11/2010 |

OTHER PUBLICATIONS

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett., 74(6):865- 867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of CHF$_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NΛCΛN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto,Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2- *b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

\* cited by examiner

Compound 1

Formula I

HOST MATERIALS FOR PHOSPHORESCENT OLEDS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds suitable for use as host materials in OLEDs, specifically compounds comprising arylgermane and arylsilane groups.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light-emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

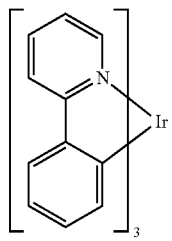

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound of Formula I is provided.

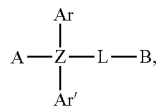

Formula I

Ar and Ar' are independently selected from the group consisting of phenyl, biphenyl, naphthyl, dibenzothiophene, and dibenzofuran, which are optionally further substituted. Z is selected from Si and Ge. L is a single bond or comprises aryl, amino, or combinations thereof, and L is optionally further substituted.

A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with at least one group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to the group directly bonded to Z.

B contains a group selected from the group consisting of carbazole, azacarbazole, and combinations thereof, which are optionally further substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole or azacarbazole group.

In one aspect, A is selected from the group consisting of:

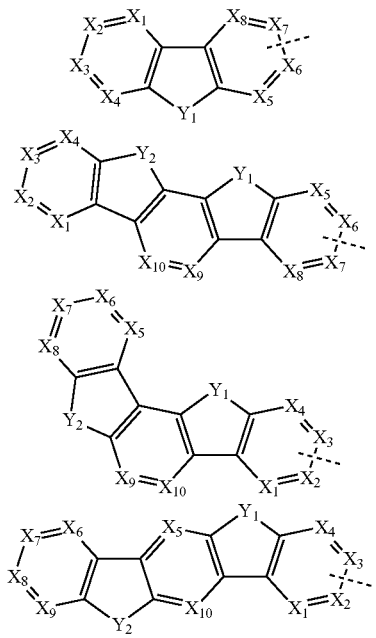

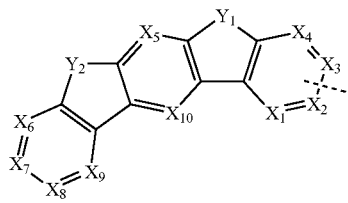

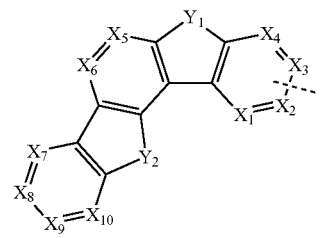

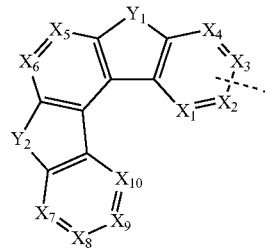

In one aspect, B is selected from the group consisting of:

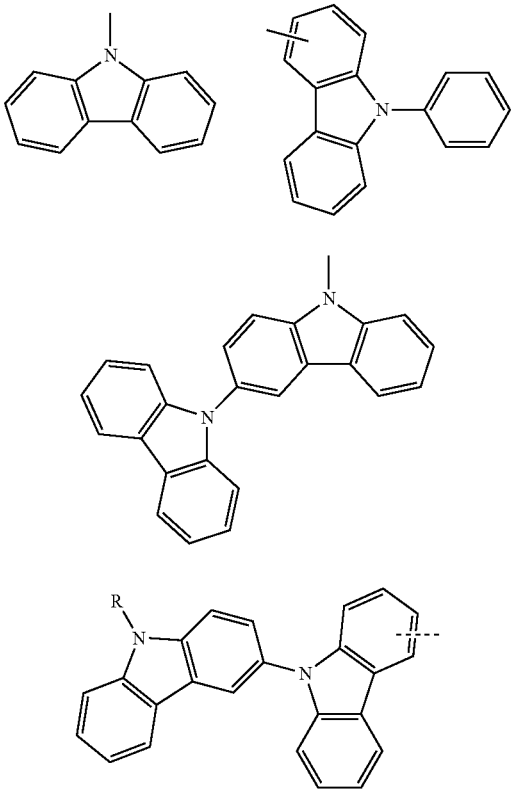

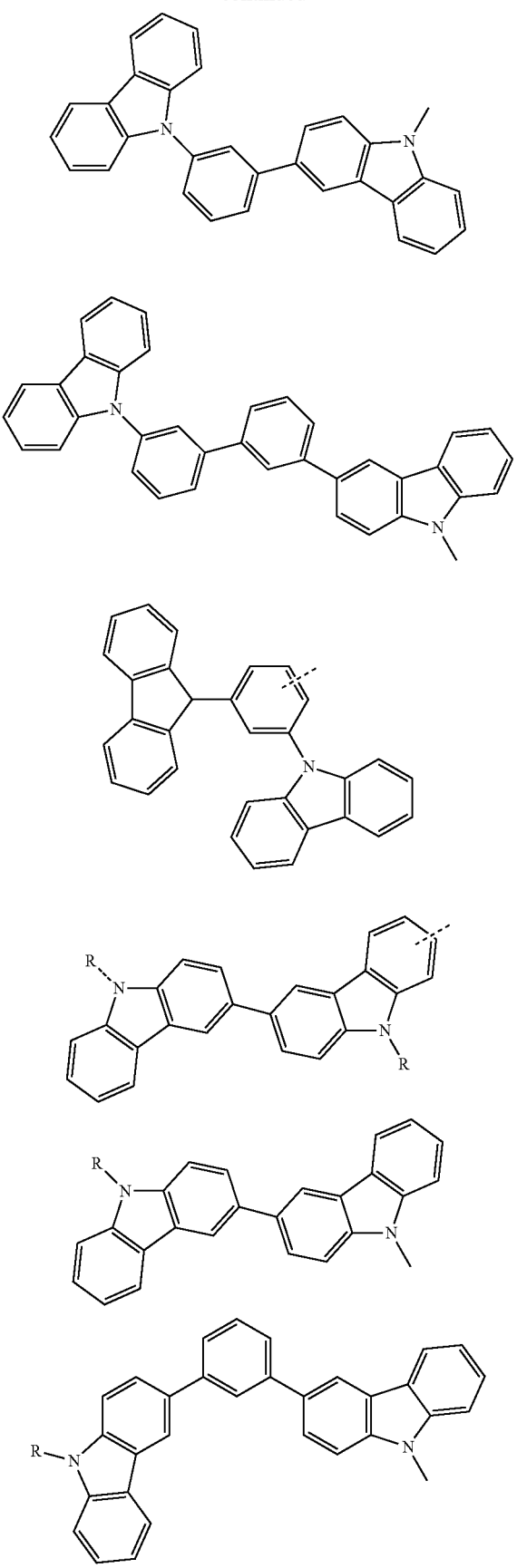
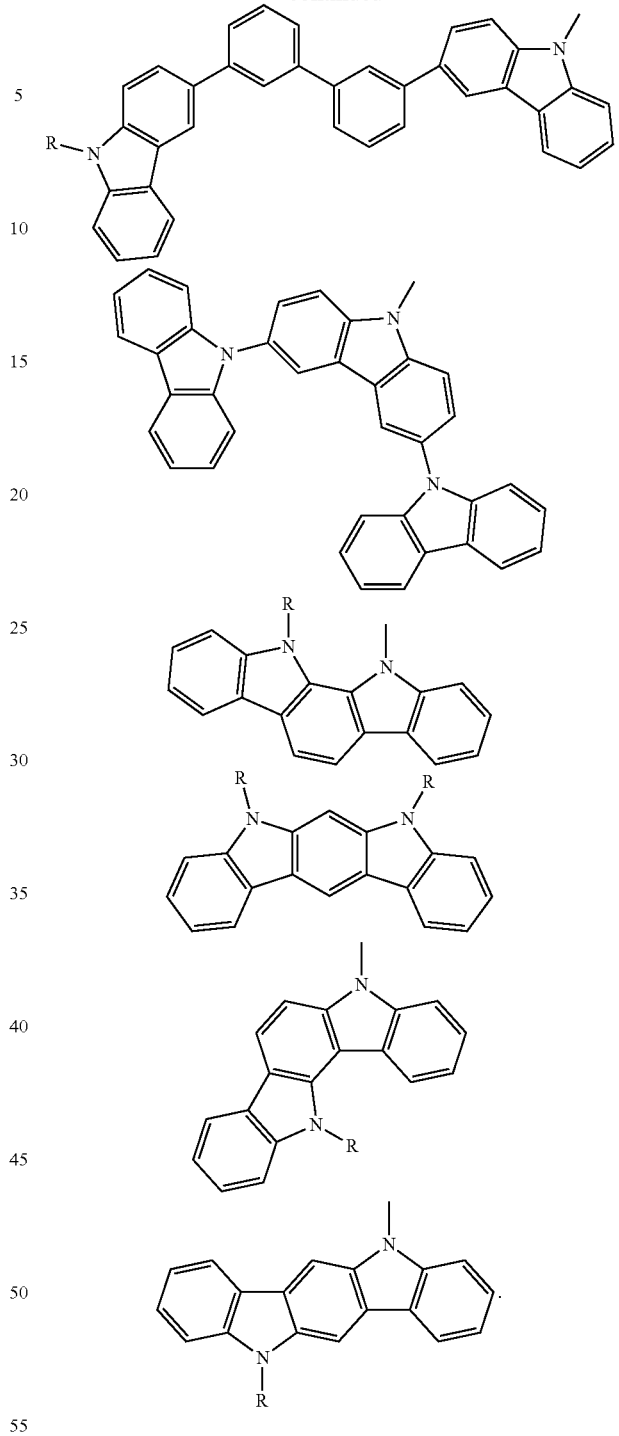

$Y_1$ and $Y_2$ are independently selected from the group consisting of O, S, and Se, $X_1$ to $X_{10}$ are independently selected from the group consisting of CR' and N, and wherein each benzo ring contains at most one N. R' is selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof. R is selected from the group consisting of hydrogen, deuterium, halide, alkyl, cycloalkyl, heteroalkyl, arylalkyl, alkoxy, aryl, heteroaryl, aryloxy, amino, and combinations thereof.

In one aspect, L is selected from the group consisting of:

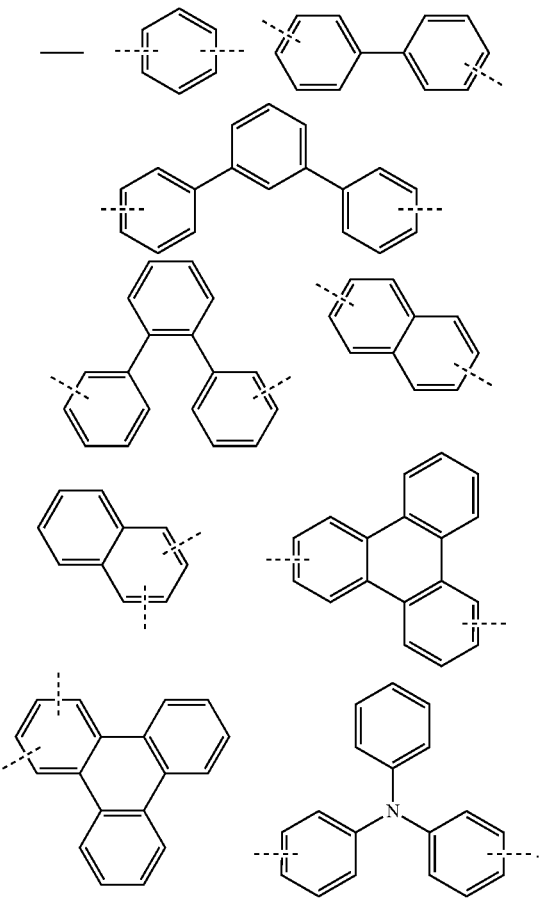

In one aspect, L is a single bond. In another aspect, L contains at least one phenyl bonded directly to Z.

In one aspect, Ar and Ar' are phenyl. In another aspect, Ar, Ar' are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound is selected from the group consisting of Compound 1-Compound 11.

A first device is provided. In one aspect, the first device comprises an organic light-emitting device, further comprising an anode, a cathode, and an organic layer, disposed between the anode and the cathode, comprising a compound having the formula:

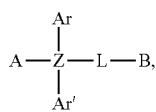

Formula I.

Ar and Ar' are independently selected from the group consisting of phenyl, biphenyl, napthyl, dibenzothiophene, and dibenzofuran, which are optionally further substituted. Z is selected from Si and Ge. L is a single bond or comprises aryl, amino, or combinations thereof, and L is optionally further substituted.

A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with at least one group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to the group directly bonded to Z.

B contains a group selected from the group consisting of carbazole, azacarbazole, and combinations thereof, which are optionally further substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole or azacarbazole group.

In one aspect, the organic layer is an emissive layer and the compound of Formula I is a host. In another aspect, the organic layer further comprises an emissive dopant. In one aspect, the emissive dopant is a transition metal complex having at least one ligand selected from the group consisting of:

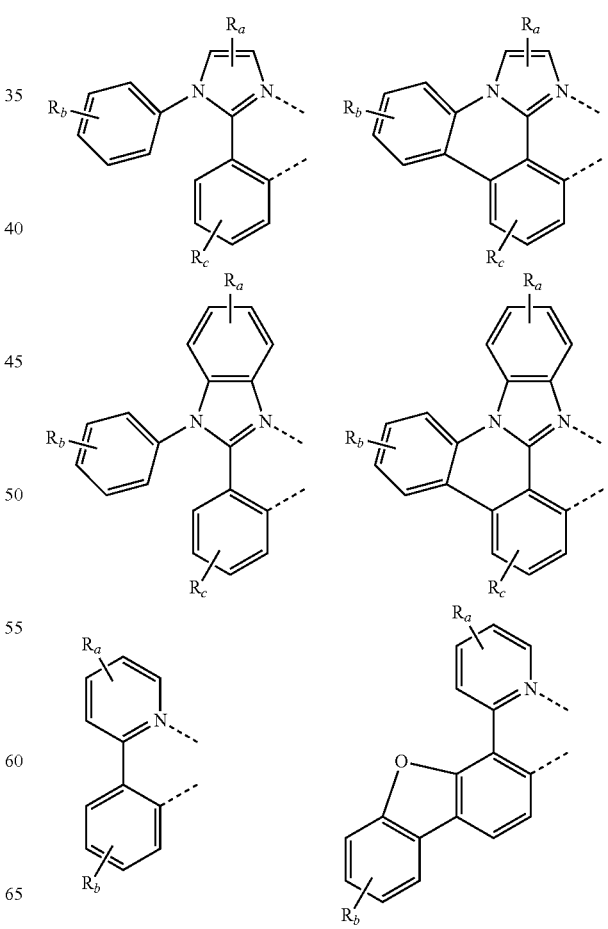

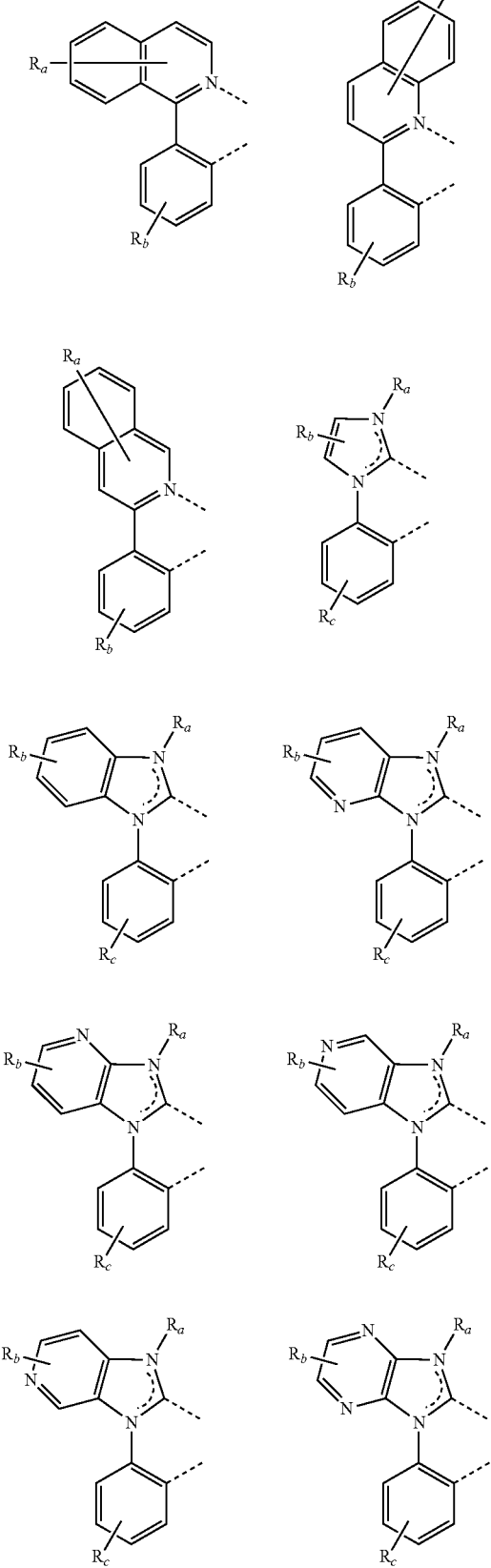

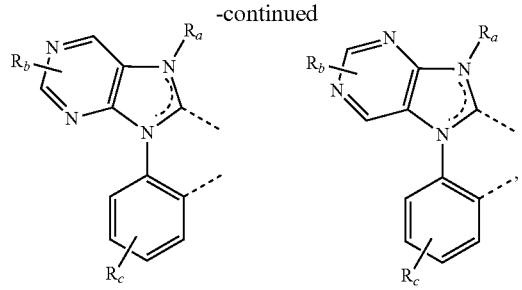

wherein $R_a$, $R_b$, and $R_c$ can represent mono, di, tri or tetra substitutions.

$R_a$, $R_b$, and $R_c$, are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, and $R_c$, are optionally joined to form a fused ring.

In one aspect the emissive dopant has the formula

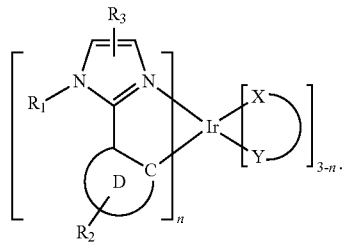

D is a 5- or 6-membered carbocyclic or heterocyclic ring and $R_1$, $R_2$, and $R_3$ independently represent mono, di, tri or tetra substitution. Each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof X—Y represents another ligand, and n is 1, 2, or 3. $R_1$ can be optionally linked to ring D.

In another aspect, the device further comprises a second organic layer that is a non-emissive layer and the compound having Formula I is a material in the second organic layer.

In one aspect, the second organic layer is a blocking layer and the compound having Formula I is a blocking material in the second organic layer.

In one aspect, the second organic layer is an electron transporting layer and the compound having the Formula I is an electron transporting material in the second organic layer.

In one aspect, the first device is a consumer product. In another aspect, the first device is an organic light-emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
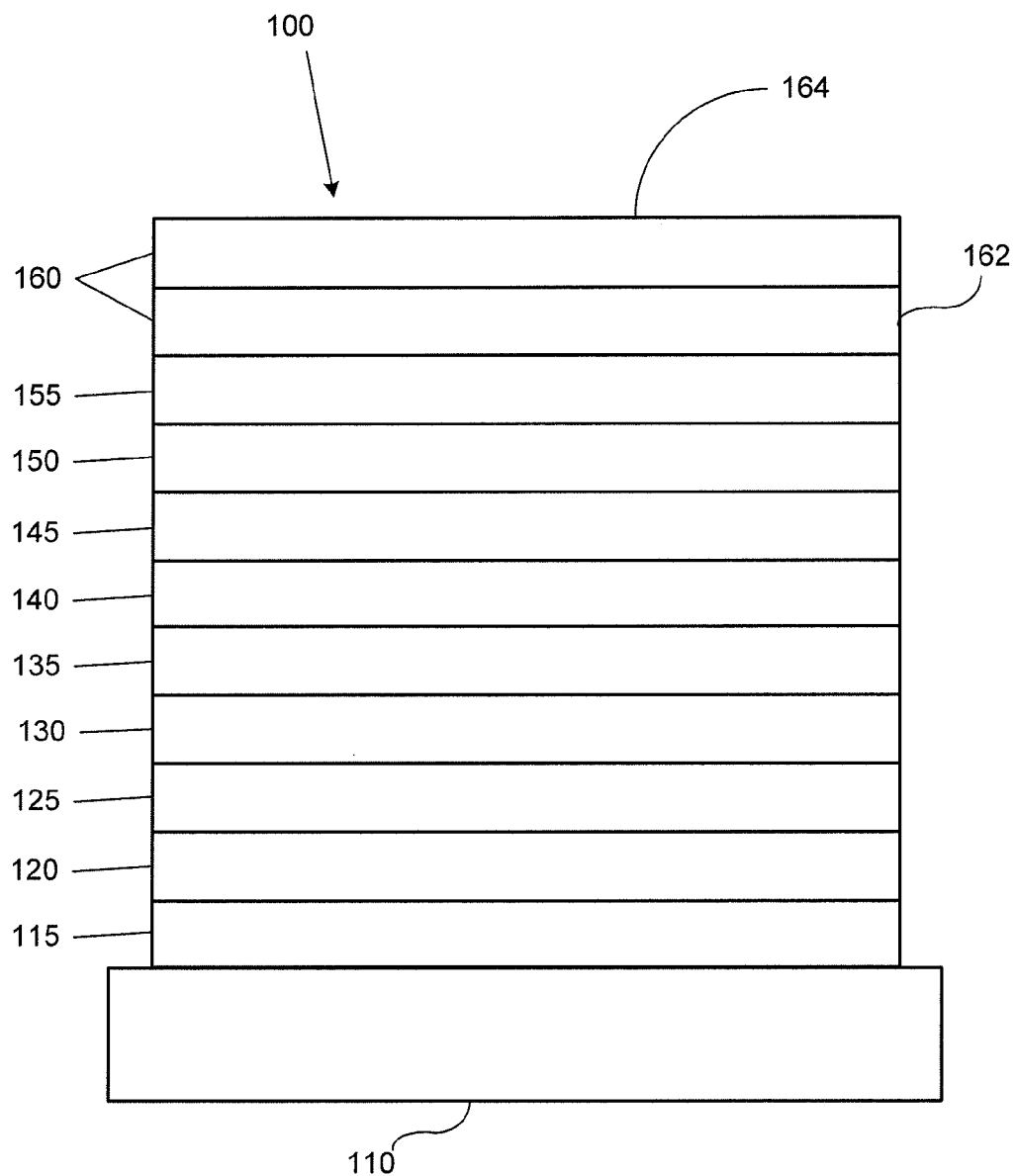
FIG. 1 shows an organic light-emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
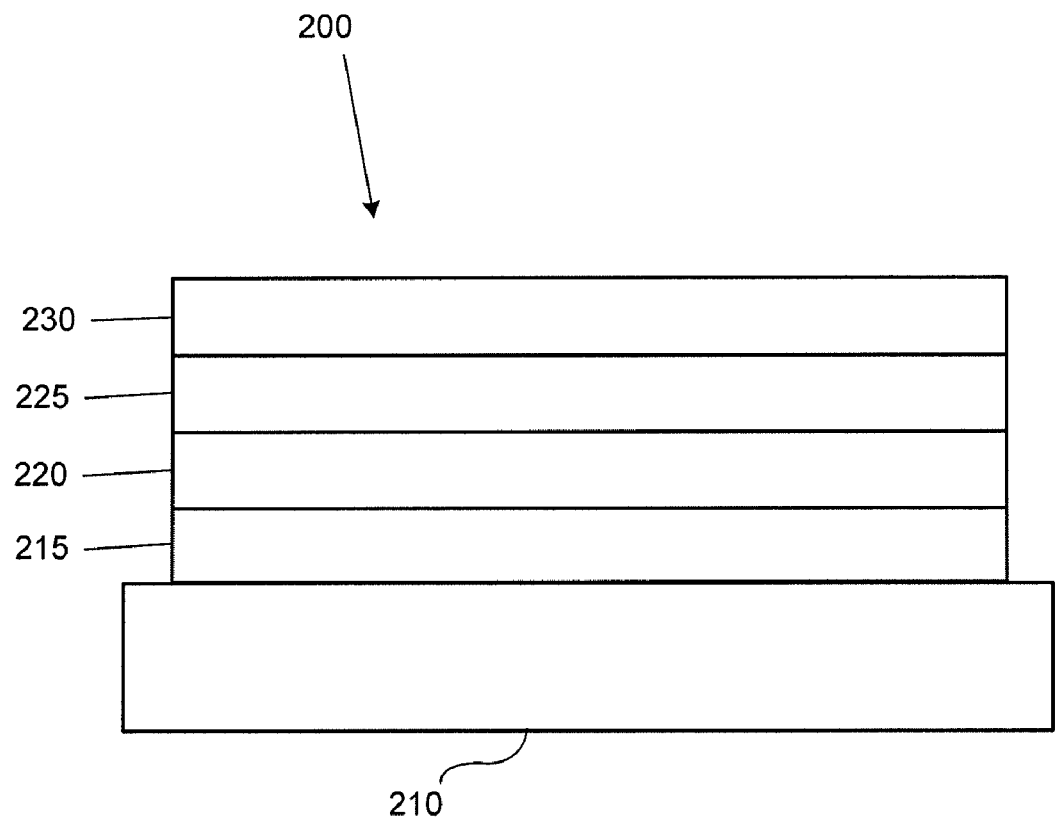
FIG. 2 shows an inverted organic light-emitting device that does not have a separate electron transport layer.
Figure 3:
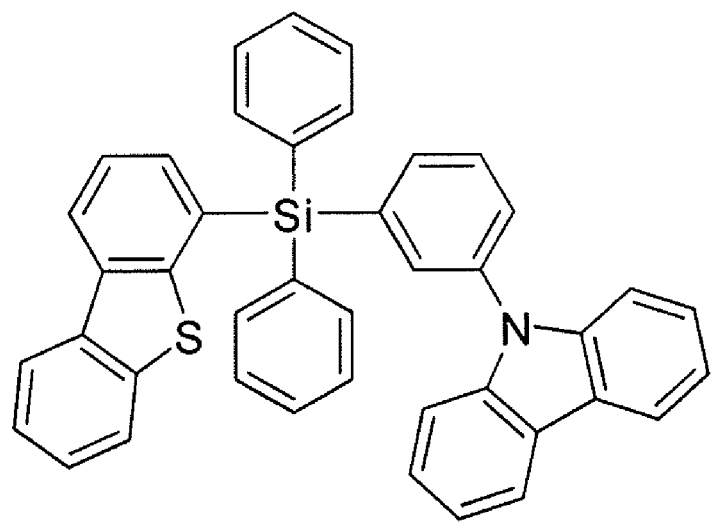
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound of Formula I is provided.

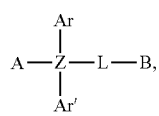

Formula I

Ar and Ar' are independently selected from the group consisting of phenyl, biphenyl, naphthyl, dibenzothiophene, and dibenzofuran, which are optionally further substituted. Z is selected from Si and Ge. L is a single bond or comprises aryl, amino, or combinations thereof, and L is optionally further substituted.

A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with at least one group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to the group directly bonded to Z.

B contains a group selected from the group consisting of carbazole, azacarbazole, and combinations thereof, which are optionally further substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof, and wherein the substitution is optionally fused to the carbazole or azacarbazole group.

An "aryl" group is an aromatic all carbon group, which can contain one or more fused rings within it. Merely by way of example, and without any limitation, exemplary aryl groups can be phenyl, naphthalene, phenanthrene, corannulene, etc. A "heteroaryl" group is an "aryl" group containing at least one heteroatom. Merely by way of example, and without any limitation, exemplary heteroaryl groups can be pyridine, quinoline, phenanthroline, azacorannulene, etc. Both "aryl" and "heteroaryl" groups can have multiple attachment points connecting them to other fragments.

In one embodiment, A is selected from the group consisting of:

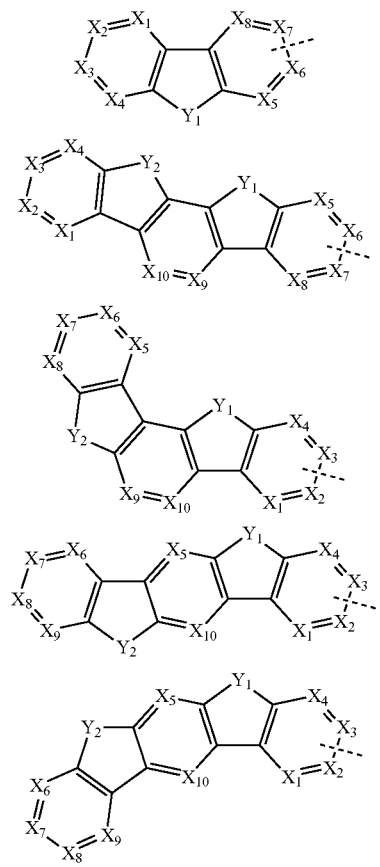

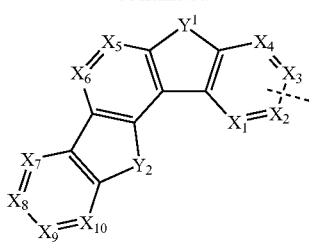
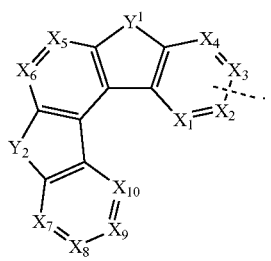
In one embodiment, B is selected from the group consisting of:
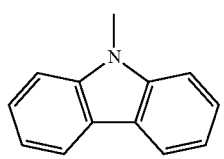
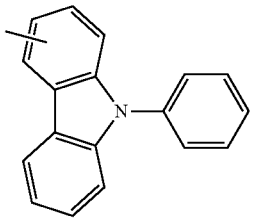
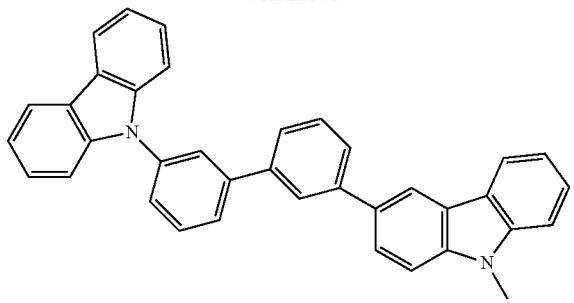
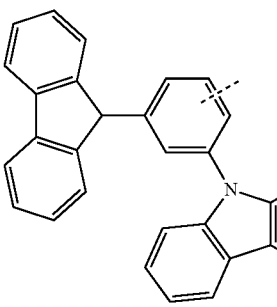
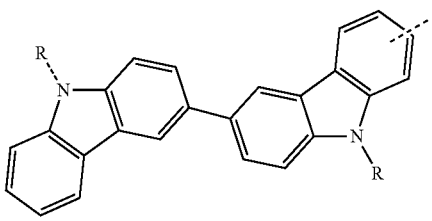
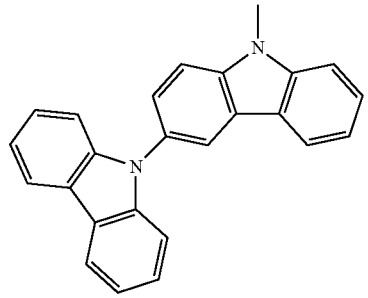
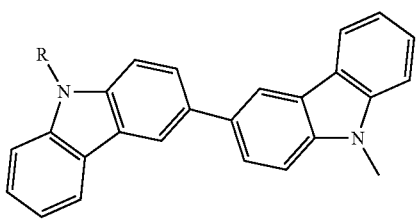
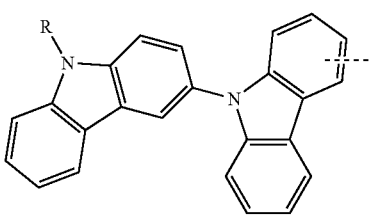
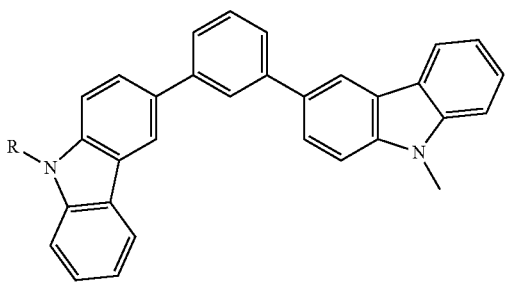
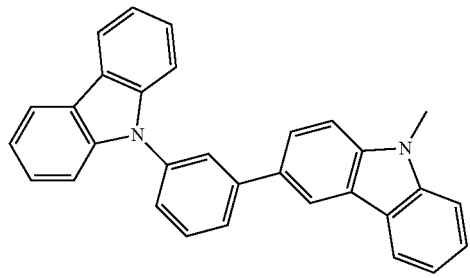
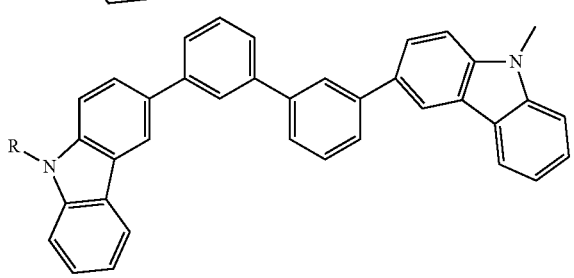

-continued

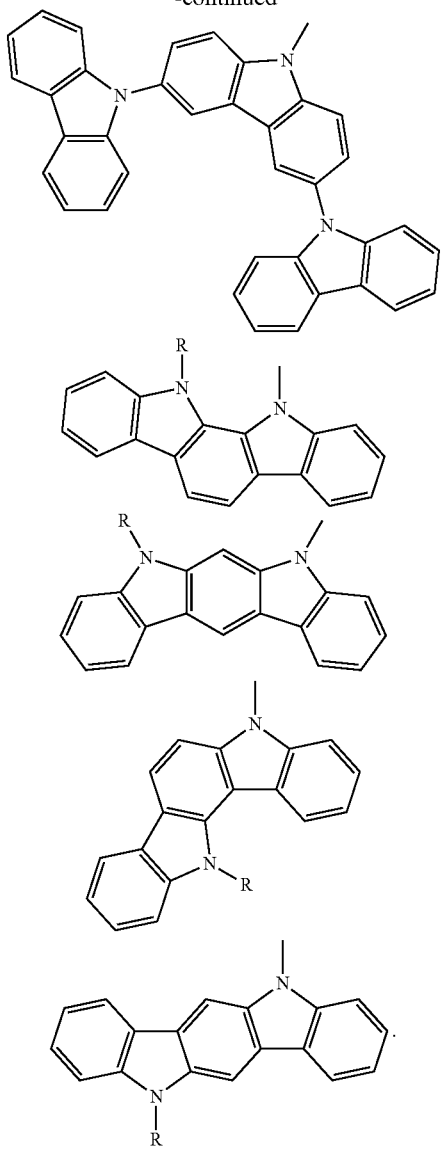

$Y_1$ and $Y_2$ are independently selected from the group consisting of O, S, and Se, $X_1$ to $X_{10}$ are independently selected from the group consisting of CR' and N, and wherein each heteroaromatic ring contains at most one N. R' is selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof. R is selected from the group consisting of hydrogen, deuterium, halide, alkyl, cycloalkyl, heteroalkyl, arylalkyl, alkoxy, aryl, heteroaryl aryloxy, amino, and combinations thereof. The dashed lines in the chemical structures disclosed herein represent a bond through any position on that group capable of forming a single bond with another atom.

In some embodiments, the A group serves as an electron transporter and the linker unit (L) and the B group serve as the hole transporter.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

As used herein, fragments containing the following structure:

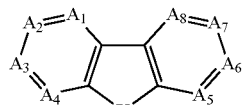

are called DBX groups, i.e. dibenzo X, where X is any of the atoms or groups described herein. In the DBX group, $A_1$-$A_8$ can comprise carbon or nitrogen.

In one embodiment, L is selected from the group consisting of:

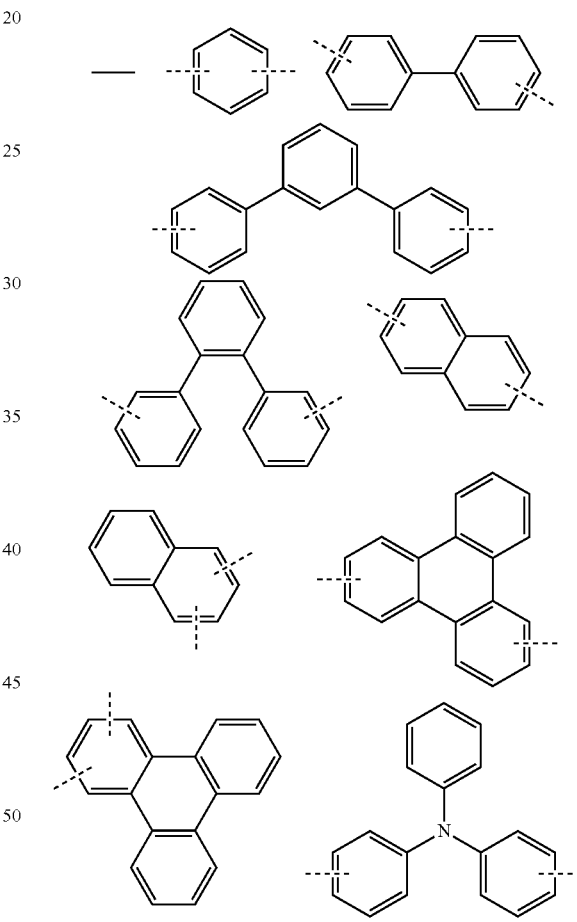

In one embodiment, L is a single bond. In another embodiment, L contains at least one phenyl bonded directly to Z.

In one embodiment, Ar and Ar' are phenyl. In another embodiment, Ar, Ar' are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

The novel compounds of Formula I disclosed herein contain of two different moieties, groups A and B, connected with an arylsilane or arylgermane spacer, resulting in an asymmetric structure. By "asymmetric" it is meant that groups A and B, as described above, have different structures. The compounds of Formula I have a number of advantageous properties when used in OLED devices. Firstly, inclusion of two distinct moieties allows fine-tuning the energy levels of the resultant compound, which may facilitate charge injection from adjacent layers and modulate charge trapping by the emitter dopants. Secondly, the two different moieties can be independently selected to have as electron and/or hole transport properties, yielding compounds with bipolar charge transport characteristics. These characteristics may not only suppresses operation voltage but also balance electron and hole fluxes to achieve an extended charge recombination zone. Thirdly, the arylsilane and arylgermane spacers break the conjugation between groups A and B, retaining high triplet energy for the entire molecule, and thus effectively reducing quenching.

The compounds of Formula I have additional advantages over known symmetric analogs because compounds of Formula I are less prone to crystallization. As a result, compounds of Formula I possess improved film uniformity, which, without being bound by theory, is believed to be a result of reduction in phase separation between the emitters and host materials in OLEDs. The novel compounds of Formula I can be used to improve OLED device performance parameters, such as emission spectrum line shape, efficiency and lifetime. Furthermore, compounds of Formula I also tend to be soluble in organic solvents such as toluene, xylene, and 3-phenoxytoluene, and are amenable to solution processing which is highly desirable for low-cost lighting applications.

In one embodiment, the compound is selected from the group consisting of:

Compound 1

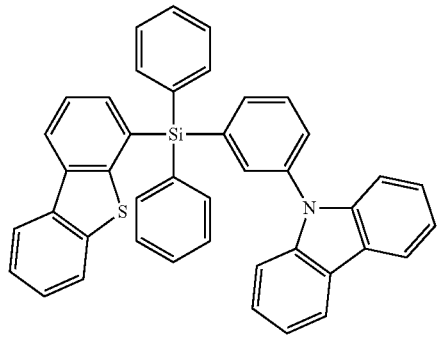

Compound 2

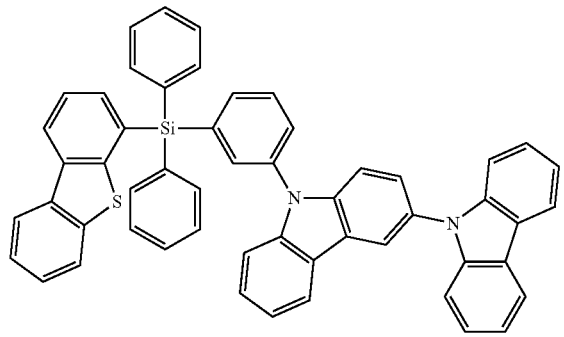

Compound 3

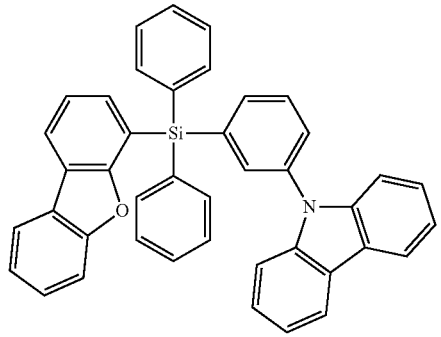

-continued
Compound 4
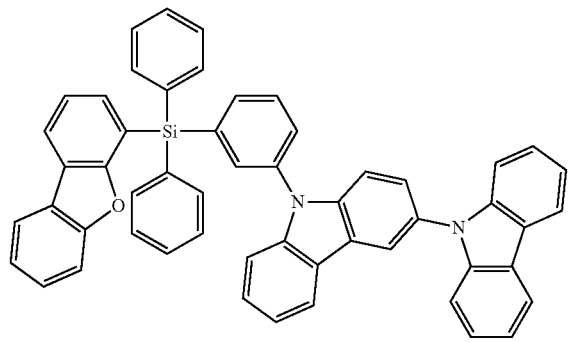
Compound 5
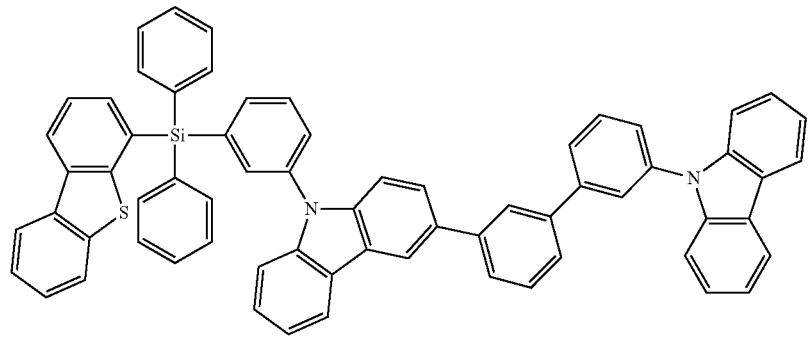
Compound 6
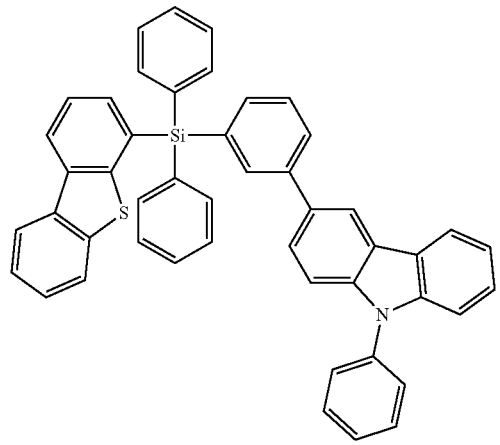
Compound 7
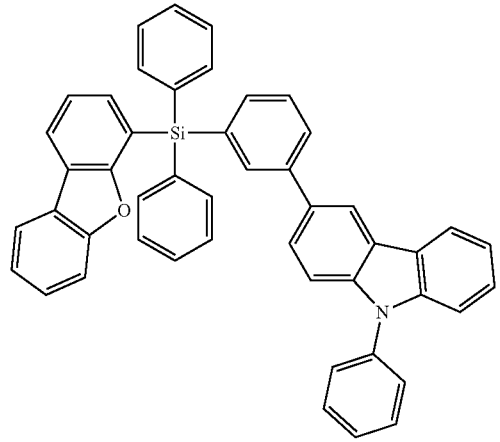

-continued

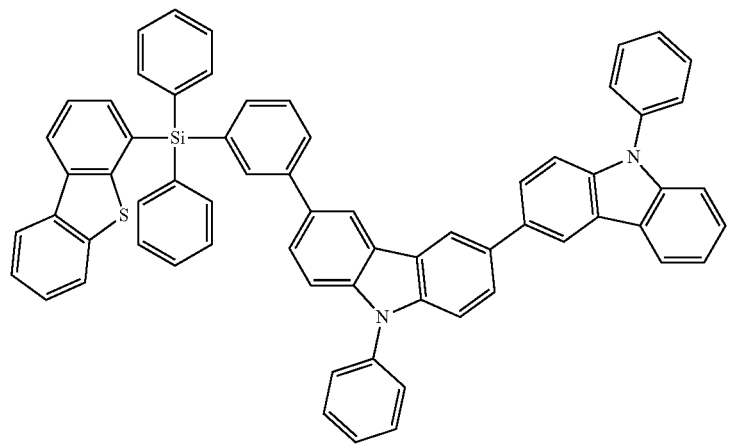

Compound 8

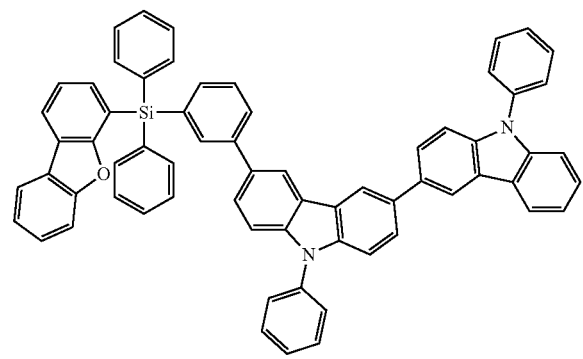

Compound 9

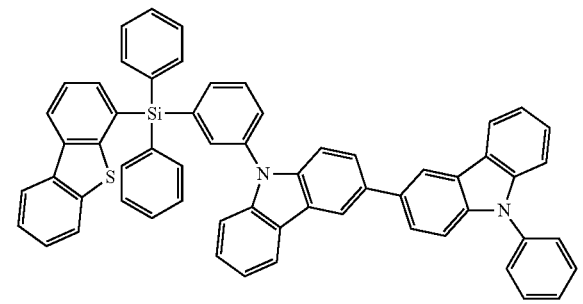

Compound 10

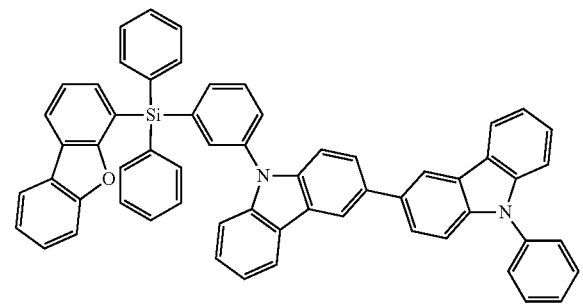

Compound 11

Table 1 lists the triplet energy levels for selected compounds of Formula I and for Comparison Compounds. The triplet energy was measured from the maximum of the highest energy 0-0 vibronic band of the phosphorescence spectra collected in $10^{-4}$M solution of the corresponding compound in 2-methyltetrahydrofuran at 77 K. Although CC-4 contains a silane unit, CC-4 has virtually the same molecular triplet energy as CC-1, 2.76 vs. 2.78 eV. In contrast, Compound 1, which has the dibenzothiophene moiety directly connected to silane unit, has a higher triplet energy of 2.99 eV, suggesting that this direct connection is able to maintain the high triplet energy of the dibenzothiophene moiety. This is further supported by Compounds 2-4, CC-2 and CC-3, which all have triplet energies of about 3.0 eV. It is noted that Compound 5 has a lower triplet energy (2.81 eV) than Compounds 1-4, which, without being bound by theory, is believed to be limited by the presence of bicarbazole groups containing a biphenylene bridge.

TABLE 1

| Compound | Triplet energy (eV) |
|---|---|
| 1 | 2.99 |
| 2 | 2.99 |
| 3 | 3.00 |
| 4 | 2.99 |
| 5 | 2.81 |
| CC-1 | 2.78 |
| CC-2 | 2.98 |
| CC-3 | 3.02 |
| CC-4 | 2.76 |

A first device is provided. In one embodiment, the first device comprises an organic light emitting device, further comprising an anode, a cathode, and an organic layer, disposed between the anode and the cathode, comprising a compound having the formula:

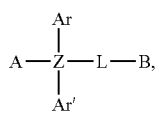

Formula I.

Ar and Ar' are independently selected from the group consisting of phenyl, biphenyl, napthyl, dibenzothiophene, and dibenzofuran, which are optionally further substituted. Z is selected from Si and Ge. L is a single bond or comprises aryl, amino, or combinations thereof, and L is optionally further substituted.

A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with a group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to at least one benzo ring of the group directly bonded to Z.

B contains a group selected from the group consisting of carbazole, azacarbazole, and combinations thereof, which are optionally further substituted with a group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole or azacarbazole group.

In one embodiment, the organic layer is an emissive layer and the compound of Formula I is a host. In another embodiment, the organic layer further comprises an emissive dopant.

In one embodiment, the emissive dopant is a transition metal complex having at least one ligand selected from the group consisting of:

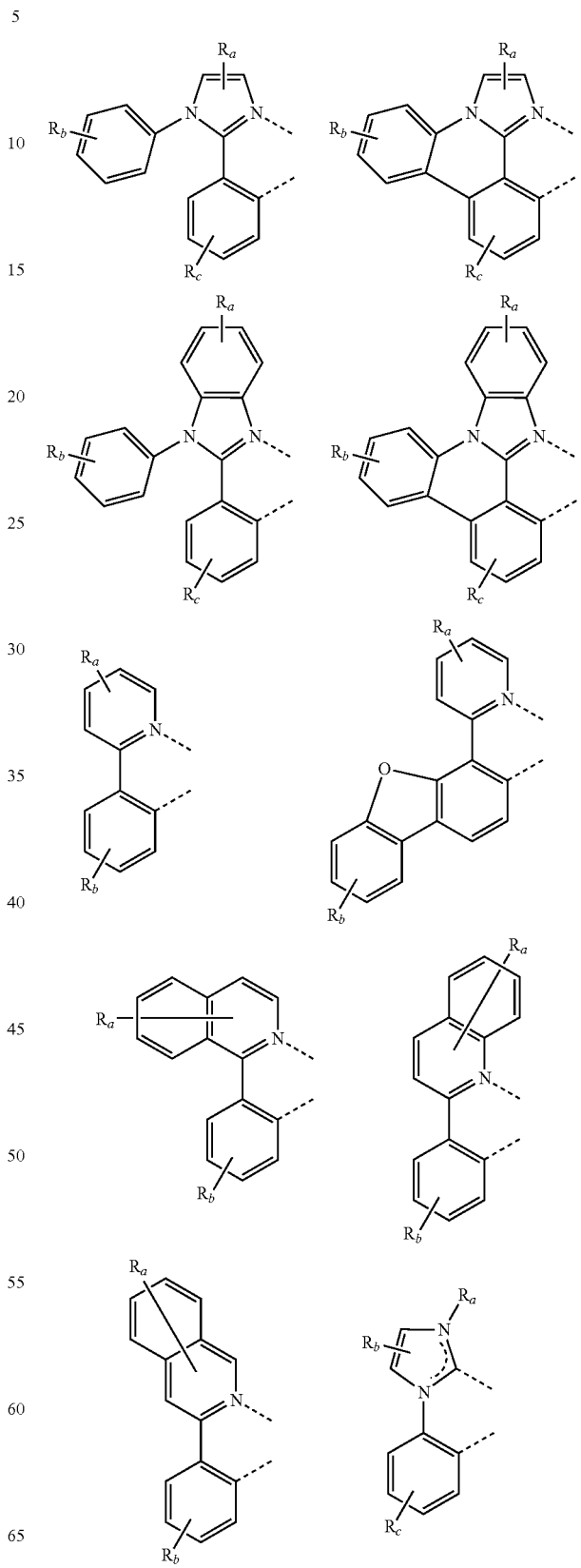

27

-continued

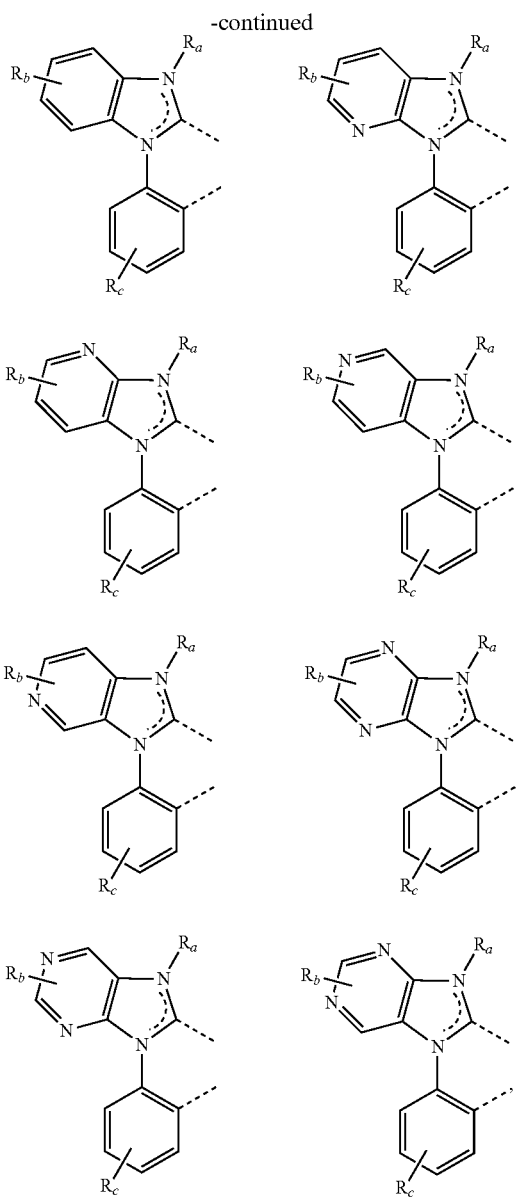

wherein $R_a$, $R_b$, and $R_c$, can represent mono, di, tri or tetra substitutions.

$R_a$, $R_b$, and $R_c$, are independently selected from the group consisting of hydrogen, deuterium, halide, alkyl, cycloalkyl, heteroalkyl, arylalkyl, alkoxy, aryloxy, amino, silyl, alkenyl,

28 cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents of $R_a$, $R_b$, and $R_c$ are optionally joined to form a fused ring.

In one embodiment the emissive dopant has the formula

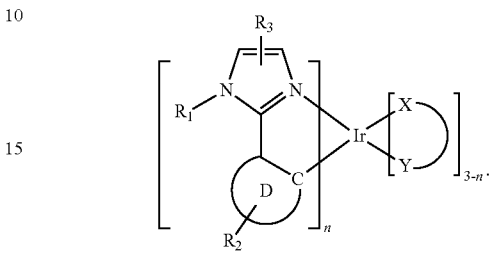

D is a 5- or 6-membered carbocyclic or heterocyclic ring and $R_1$, $R_2$, and $R_3$ independently represent mono, di, tri or tetra substitution. Each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. X—Y represents another ligand, and n is 1, 2, or 3. $R_1$ can be optionally linked to ring D.

In another embodiment, the device further comprises a second organic layer that is a non-emissive layer and the compound having Formula I is a material in the second organic layer.

In one embodiment, the second organic layer is a blocking layer and the compound having Formula I is a blocking material in the second organic layer.

In one embodiment, the second organic layer is an electron transporting layer and the compound having the Formula I is an electron transporting material in the second organic layer.

In one embodiment, the first device is a consumer product. In another embodiment, the first device is an organic light-emitting device.

Device Examples

The structures of the materials used in the device examples are shown below:

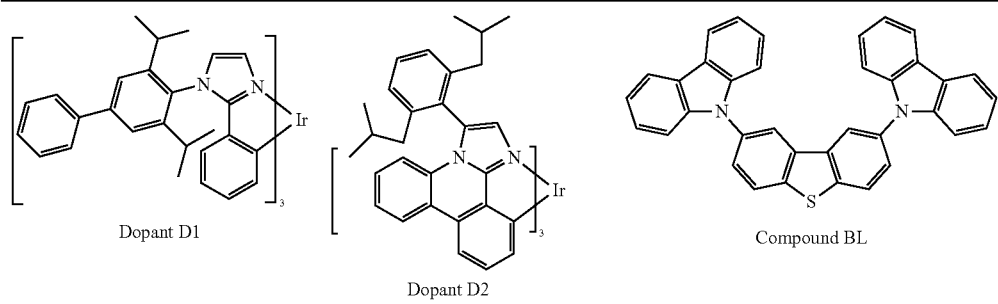

Dopant D1

Dopant D2

Compound BL

-continued

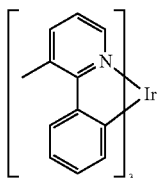
Compound HIL

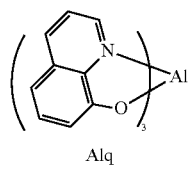
Alq

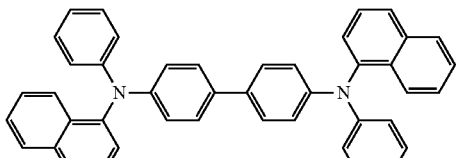
Compound NPD

The structures of the Comparative Compounds described herein are as follows:

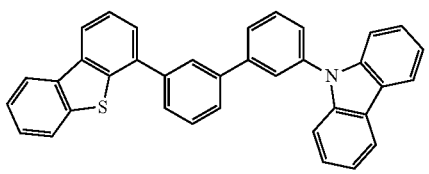
CC-1

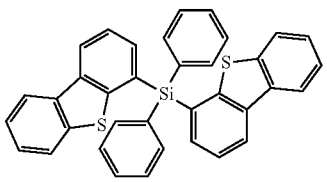
CC-2

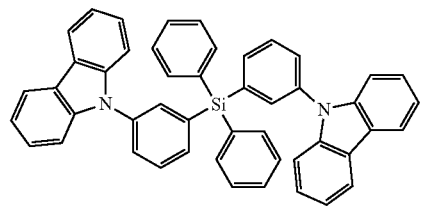
CC-3

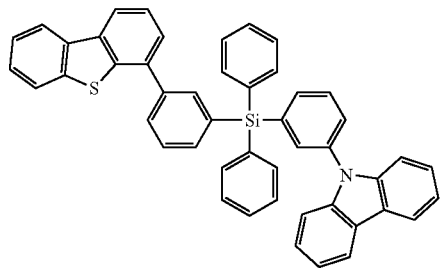
CC-4

All example devices were fabricated by high vacuum ($<10^{-7}$ Torr) thermal evaporation (VTE). The anode electrode is 800 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Figure 4:
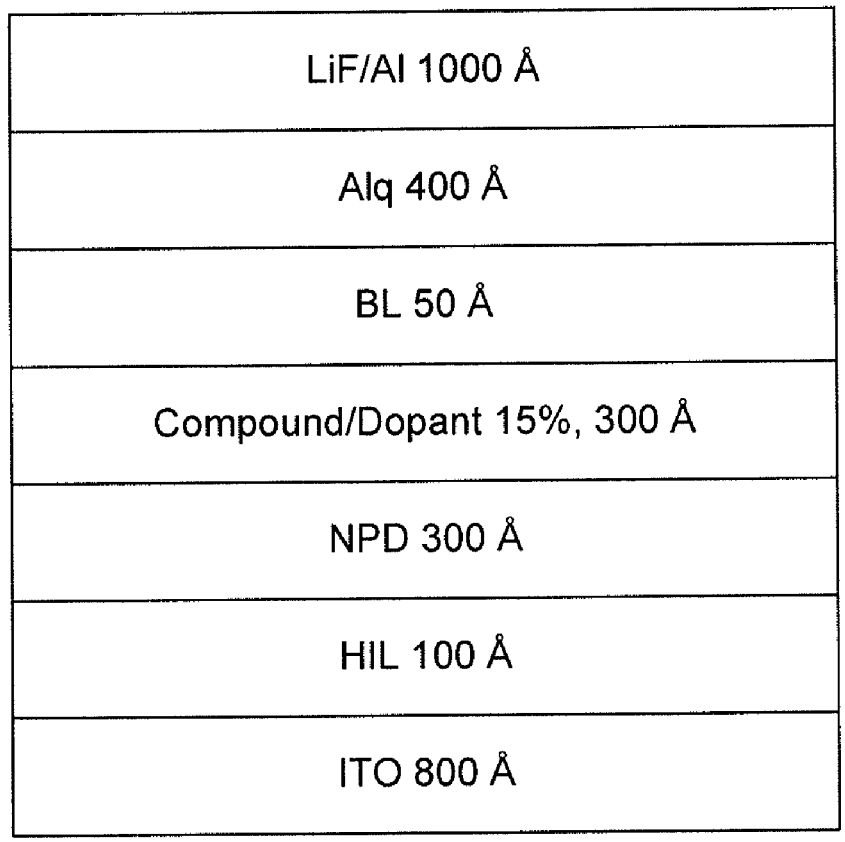
FIG. 4 shows a sample OLED device structure incorporating compounds of Formula I.

The organic stack of the OLED device used in the Examples and Comparative Device Examples has the following structure: from the ITO surface, 100 Å of Compound HIL as the hole injection layer, 300 Å of NPD as the hole transporting layer (HTL), 300 Å of a compound of Formula I (CC-1, CC-2, CC-3, or CC-4 doped with 15 weight percent of Dopant D1 or Dopant D2 as the emissive layer (EML), 50 Å of Compound BL or a compound of Formula I as the Blocking Layer (BL) and 400 Å of Alq as the electron transporting layer (ETL). The device structure is shown in FIG. 4.

TABLE 2

| Example | Host | Dopant | BL | 1931 CIE x | 1931 CIE y | $\lambda_{max}$ [nm] | At 1000 nits LE [cd/A] | At 1000 nits EQE [%] | At 1000 nits PE [lm/W] | At 20 mA/cm² $LT_{80\%}$ [h] |
|---|---|---|---|---|---|---|---|---|---|---|
| Device Example 1 | Compound 1 | Dopant D1 | Compound BL | 0.177 | 0.390 | 474 | 43.5 | 19.2 | 20.0 | 73 |
| Device Example 2 | Compound 2 | Dopant D1 | Compound BL | 0.175 | 0.387 | 474 | 43.9 | 19.6 | 21.2 | 76 |
| Device Example 3 | Compound 3 | Dopant D1 | Compound BL | 0.175 | 0.382 | 474 | 43.4 | 19.5 | 21.0 | 63 |
| Device Example 4 | Compound 4 | Dopant D1 | Compound BL | 0.179 | 0.404 | 474 | 43.1 | 18.7 | 21.0 | 73 |
| Device Example 5 | Compound 5 | Dopant D1 | Compound BL | 0.177 | 0.399 | 474 | 47.2 | 20.6 | 22.1 | 53 |

TABLE 2-continued

| | | | | 1931 CIE | | $\lambda_{max}$ | At 1000 nits | | | At 20 mA/cm² |
|---|---|---|---|---|---|---|---|---|---|---|
| | | | | | | | LE | EQE | PE | $LT_{80\%}$ |
| Example | Host | Dopant | BL | x | y | [nm] | [cd/A] | [%] | [lm/W] | [h] |
| Device Example 6 | Compound 1 | Dopant D1 | Compound 1 | 0.174 | 0.382 | 474 | 41.8 | 18.8 | 16.6 | 66 |
| Device Example 7 | Compound 2 | Dopant D1 | Compound 2 | 0.173 | 0.383 | 474 | 36.7 | 16.5 | 14.9 | 58 |
| Device Example 8 | Compound 3 | Dopant D1 | Compound 3 | 0.170 | 0.371 | 474 | 39.8 | 18.2 | 18.4 | 49 |
| Device Example 9 | Compound 4 | Dopant D1 | Compound 4 | 0.177 | 0.399 | 474 | 38.0 | 16.6 | 15.2 | 63 |
| Device Example 10 | Compound 5 | Dopant D1 | Compound 5 | 0.176 | 0.395 | 474 | 43.0 | 19.0 | 17.3 | 53 |
| Comparative Device Example 1 | Compound CC-1 | Dopant D1 | Compound BL | 0.179 | 0.396 | 474 | 35.4 | 15.4 | 15.5 | 176 |
| Comparative Device Example 2 | Compound CC-2 | Dopant D1 | Compound BL | 0.178 | 0.396 | 474 | 46.1 | 20.1 | 21.6 | 34 |
| Comparative Device Example 3 | Compound CC-3 | Dopant D1 | Compound BL | 0.177 | 0.388 | 474 | 42.9 | 18.9 | 19.8 | 40 |
| Comparative Device Example 4 | Compound CC-4 | Dopant D1 | Compound BL | 0.172 | 0.376 | 474 | 43 | 19.6 | 20.2 | 86 |

Table 2 is a summary of the device data. where Dopant D1 is the emitter The luminous efficiency (LE), external quantum efficiency (EQE) and power efficiency (PE) were measured at 1000 nits, while the lifetime ($LT_{80\%}$) was defined as the time required for the device to decay to 80% of its initial luminance under a constant current density of 20 mA/cm². In some embodiments, the compounds containing a silane bridge demonstrate higher efficiency, e.g. Device Examples 1-5 and Comparative Device Examples 2 and 3 compared to Comparative Device Example 1. Without being bound by theory, these results are attributable in part to the breakage of conjugation by the silane bridge and retention of high triplet energy for individual molecules. Additionally, the steric hindrance introduced by the tetraphenylsilane unit can also prevent unfavorable intermolecular stacking that can decrease the triplet energy in the solid state. A high triplet energy of the host effectively confines the excitons on emitters, leading to high efficiency.

Additionally, devices with the asymmetric silane hosts (i.e. compounds of Formula I with Z=Si) containing both DBX and carbazole moieties have improved lifetimes than those with the symmetric silane hosts (Device Examples 1-5 vs. Comparative Device Examples 2 and 3). Device Examples 1, 2 and 4 have twice the lifetimes of Comparative Device Example 2. This increase in lifetime is attributable to the bipolar nature of the compounds of Formula I, which helps to balance charge fluxes. Without being bound by theory, it is believed that the balanced electron/hole fluxes spread the charge recombination zone, which preserves a high efficiency at high brightness by suppressing or reducing exciton quenching. An expanded charge recombination zone also extends the device lifetime by allowing a larger population of molecules to have charge transport, exciton formation, and light emission roles. Furthermore, compounds of Formula I can also be used in the hole blocking layers, as illustrated in Device Examples 6-10. Since compounds of Formula I can serve both as hosts and hole blocking materials in the hole blocking layers, incorporation of these materials into optical devices is expected to reduce device fabrication cost.

TABLE 3

| | | | | 1931 CIE | | $\lambda_{max}$ | At 1000 nits | | | At 2000 nits |
|---|---|---|---|---|---|---|---|---|---|---|
| | | | | | | | LE | EQE | PE | $LT_{80\%}$ |
| Example | Host | Dopant | BL | x | y | [nm] | [cd/A] | [%] | [lm/W] | [h] |
| Device Example 11 | Compound 1 | Dopant D2 | Compound BL | 0.154 | 0.240 | 462 | 24.2 | 14.5 | 12.4 | 32 |
| Device Example 12 | Compound 2 | Dopant D2 | Compound BL | 0.155 | 0.238 | 462 | 22.6 | 13.6 | 11.9 | 23 |
| Device Example 13 | Compound 3 | Dopant D2 | Compound BL | 0.153 | 0.237 | 462 | 23.3 | 14.1 | 11.9 | 23 |
| Device Example 14 | Compound 4 | Dopant D2 | Compound BL | 0.155 | 0.232 | 462 | 21.4 | 13.1 | 10.9 | 20 |

It is noted that Compounds 1-4 have high triplet energies and are suitable as hosts for deeper blue emitters. For illustration, Table 3 is a summary of the device data where the emissive layer comprises of a compound of Formula I doped with 15 weight percent of Dopant D2. The luminous efficiency (LE), external quantum efficiency (EQE) and power efficiency (PE) were measured at 1000 nits, while the lifetime ($LT_{80\%}$) was defined as the time required for the device to decay to 80% of its initial luminance of 2000 nits under a constant current density.

Device Examples 11-14 also show good efficiencies, indicating that the triplet energy of the host is sufficiently high so as not to quench the emission of the deeper blue dopant.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

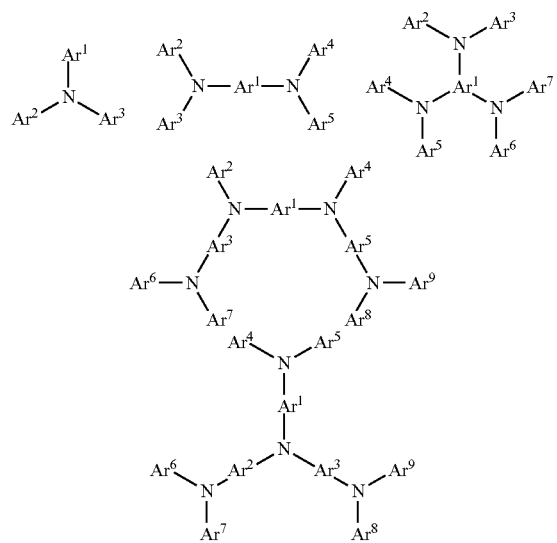

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $Ar^1$ to $Ar^9$ is independently selected from the group consisting of:

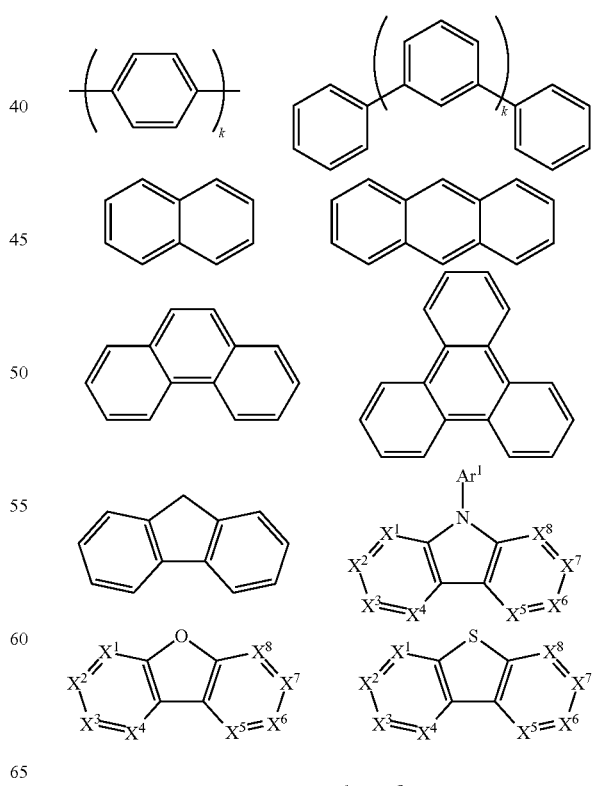

k is an integer from 1 to 20; $X^1$ to $X^8$ is C (including CH) or N; $Ar^1$ has the same group defined above.

Examples of metal complexes used in HIL or HTL include, but not limit to the following general formula:

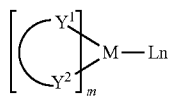

M is a metal, having an atomic weight greater than 40; ($Y^1$—$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$—$Y^2$) is a 2-phenylpyridine derivative.
In another aspect, ($Y^1$—$Y^2$) is a carbene ligand.
In another aspect, M is selected from Ir, Pt, Os, and Zn.
In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

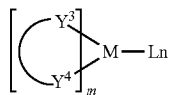

M is a metal; ($Y^3$—$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

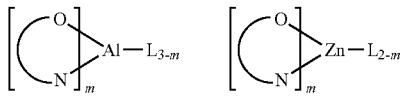

(O—N) is a bidentate ligand, having metal coordinated to atoms O and N.

In another aspect, M is selected from Ir and Pt.
In a further aspect, ($Y^3$—$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

In one aspect, host compound contains at least one of the following groups in the molecule:

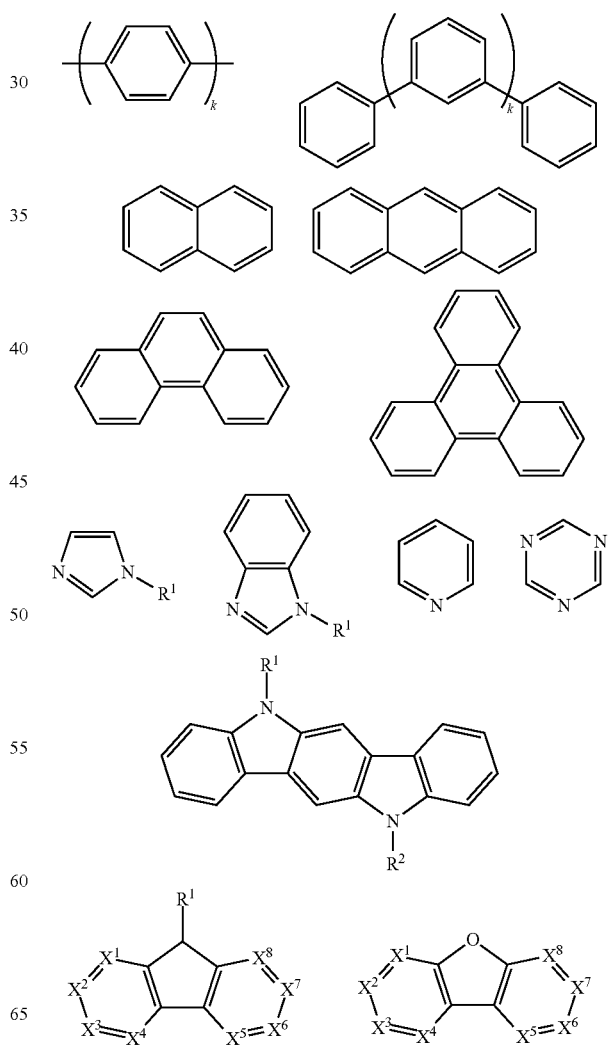

-continued

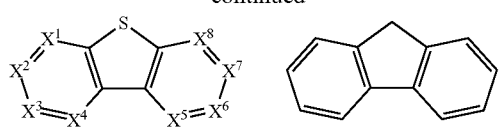

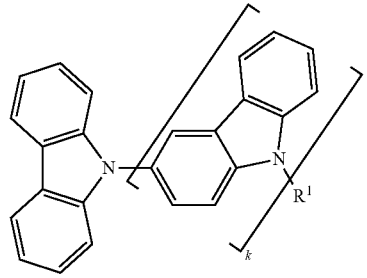

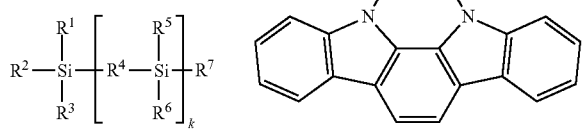

R¹ to R⁷ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X¹ to X⁸ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

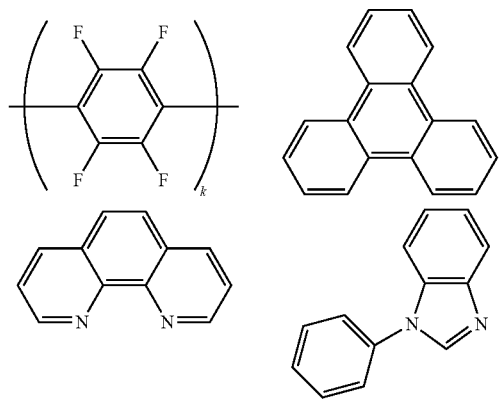

-continued

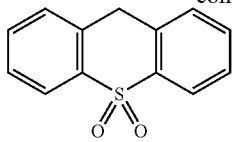

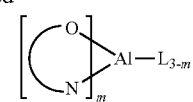

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

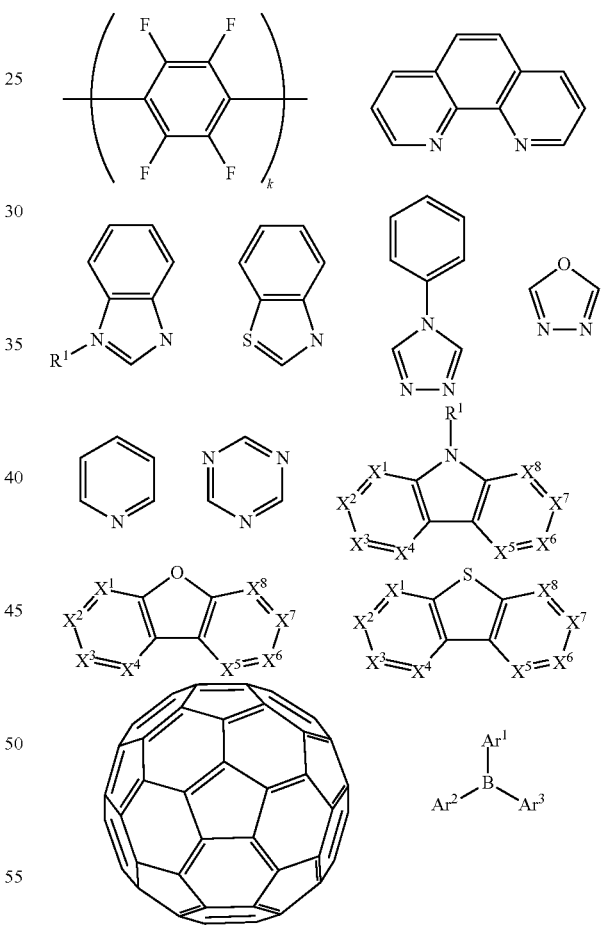

R¹ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

Ar¹ to Ar³ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

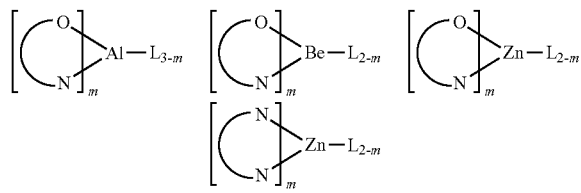

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluoro-hydrocarbon polymer | $-\!\!\left[CH_xF_y\right]_n\!\!-$ | Appl. Phys. Lett. 78, 673 (2001) |

TABLE 4-continued
| MATERIAL | EXAMPLES OF MATERIAL | PUBLICATIONS |
|---|---|---|
| Conducting polymers (e.g., PEDOT:PSS, polyaniline, polypthiophene) | 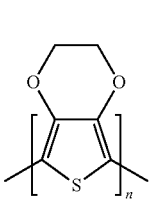 | Synth. Met. 87, 171 (1997) WO2007002683 |
| Phosphonic acid and sliane SAMs | 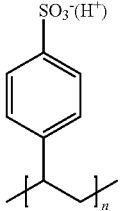 | US20030162053 |
| Triarylamine or polythiophene polymers with conductivity dopants | 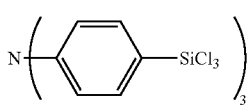 and 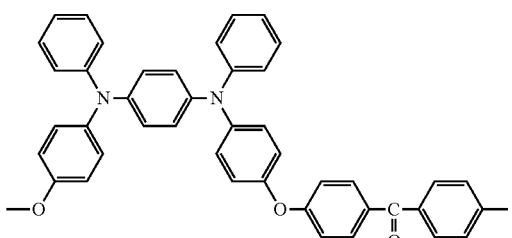 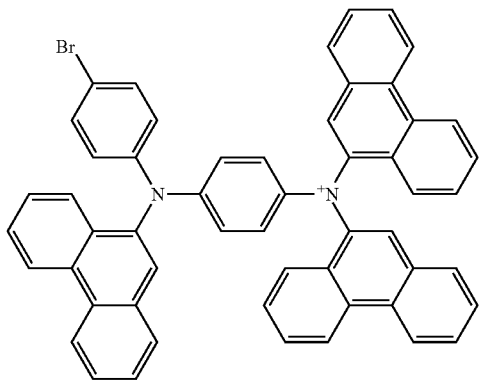 | EP1725079A1 |

TABLE 4-continued
| MATERIAL | EXAMPLES OF MATERIAL | PUBLICATIONS |
|---|---|---|
| Arylamines complexed with metal oxides such as molybdenum and tungsten oxides | 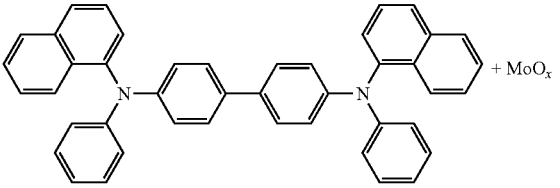 [SMILES: c1ccc(N(c2ccc(-c3ccc(N(c4ccccc4)c4cccc5ccccc45)cc3)cc2)c2cccc3ccccc23)cc1] + MoO$_x$ | SID Symposium Digest, 37, 923 (2006) WO2009018009 |
| p-type semiconducting organic complexes | 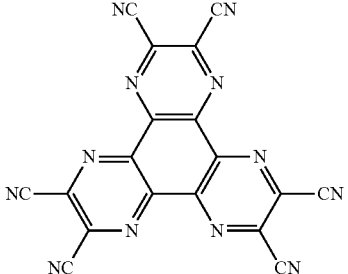 [SMILES: N#Cc1nc2c3nc(C#N)c(C#N)nc3c3nc(C#N)c(C#N)nc3c2nc1C#N] | US20020158242 |
| Metal organometallic complexes | 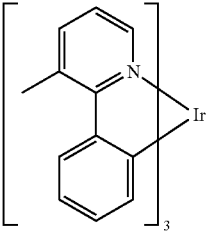 | US20060240279 |
| Cross-linkable compounds | 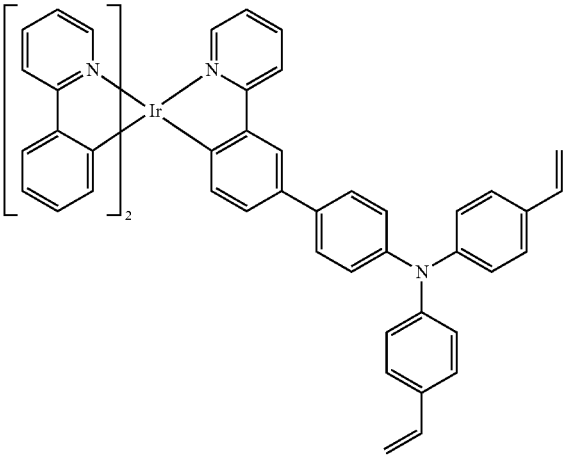 | US20080220265 |
Hole transporting materials
| | | |
|---|---|---|
| Triarylamines (e.g., TPD, α-NPD) | 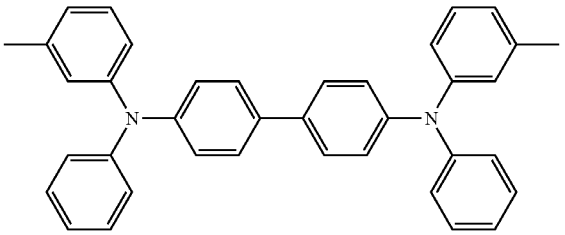 | Appl. Phys. Lett. 51, 913 (1987) |

TABLE 4-continued

| MATERIAL | EXAMPLES OF MATERIAL | PUBLICATIONS |
|---|---|---|
| | | US5061569 |
| | | EP650955 |
| | | J. Mater. Chem. 3, 319 (1993) |
| | | Appl. Phys. Lett. 90, 183503 (2007) |

TABLE 4-continued
| MATERIAL | EXAMPLES OF MATERIAL | PUBLICATIONS |
|---|---|---|
| | 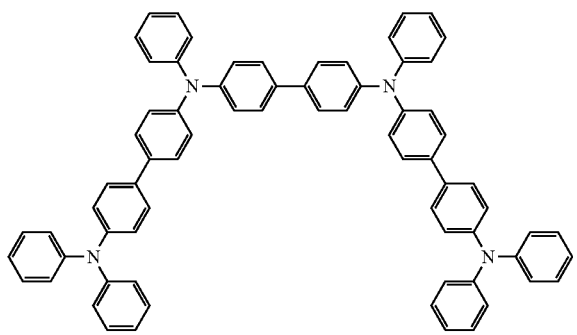 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 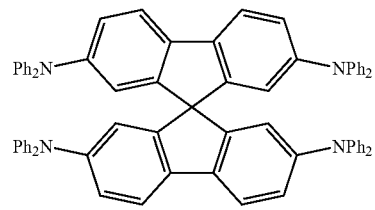 | Synth. Met. 91, 209 (1997) |
| Arylamine carbazole compounds | 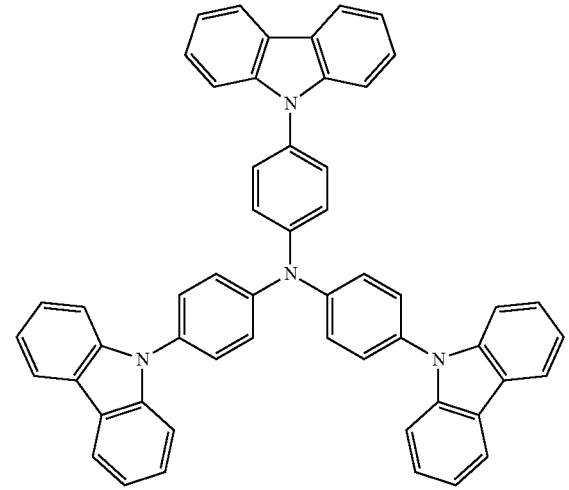 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/ (di)benzofuran | 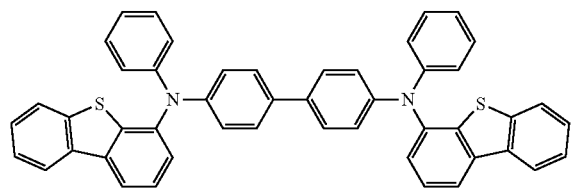 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |

TABLE 4-continued
| MATERIAL | EXAMPLES OF MATERIAL | PUBLICATIONS |
|---|---|---|
| Indolocarbazoles | 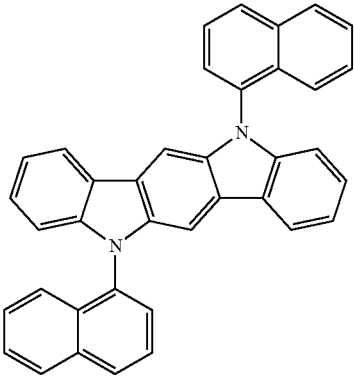 [SMILES: c1ccc2c(-n3c4ccccc4c4cc5c(cc43)c3ccccc3n5-c3cccc4ccccc34)cccc2c1] | Synth. Met. 111,421 (2000) |
| Isoindole compounds | 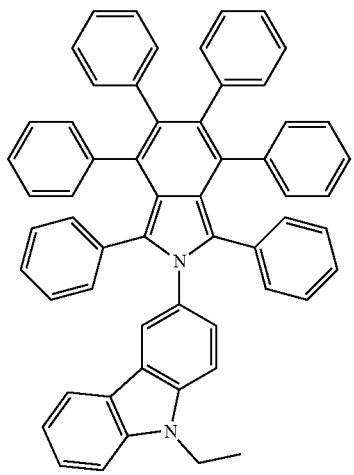 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15,3148 (2003) |
| Metal carbene complexes | 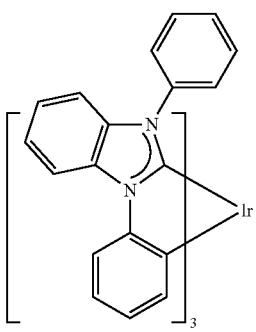 | US20080018221 |
Phosphorescent OLED host materials
Red hosts
| Arylcarbazoles | 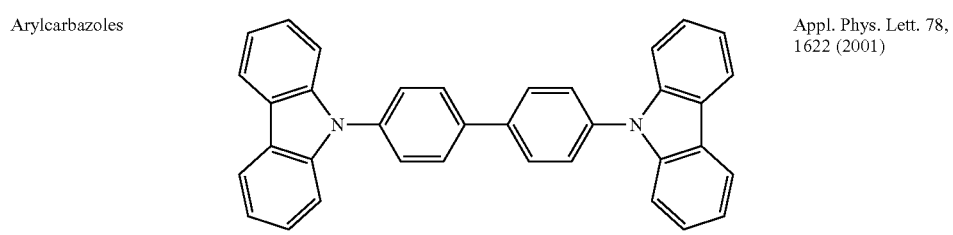 | Appl. Phys. Lett. 78, 1622 (2001) |

TABLE 4-continued

| MATERIAL | EXAMPLES OF MATERIAL | PUBLICATIONS |
|---|---|---|
| Metal 8-hydroxy-quinolates (e.g.,Alq$_3$, BAlq) | | Nature 395, 151 (1998) |
| | | US20060202194 |
| | | WO2005014551 |
| | | WO2006072002 |
| Metal phenoxy-benzothiazole compounds | | Appl. Phys. Lett. 90, 123509(2007) |
| Conjugated oligomers and polymers (e.g.. polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 4-continued

| MATERIAL | EXAMPLES OF MATERIAL | PUBLICATIONS |
|---|---|---|
| Zinc complexes | | WO2009062578 |"
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 4-continued
| MATERIAL | EXAMPLES OF MATERIAL | PUBLICATIONS |
|---|---|---|
| | 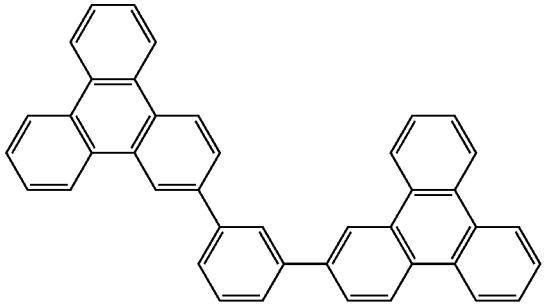 [SMILES: c1cc(-c2ccc3c4ccccc4c4ccccc4c3c2)cc(-c2ccc3c4ccccc4c4ccccc4c3c2)c1] | US20060280965 |
| | 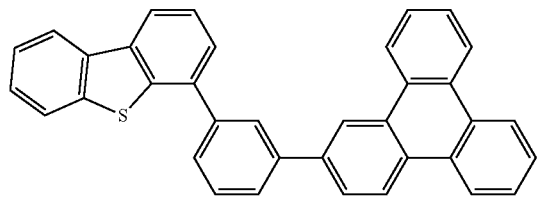 [SMILES: c1cc(-c2ccc3c4ccccc4c4ccccc4c3c2)cc(-c2cccc3c2sc2ccccc23)c1] | WO2009021126 |
| Donor acceptor type molecules | 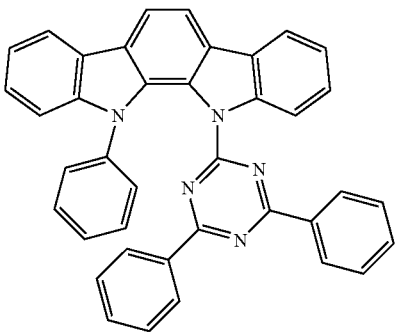 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/ DBT/DBF | 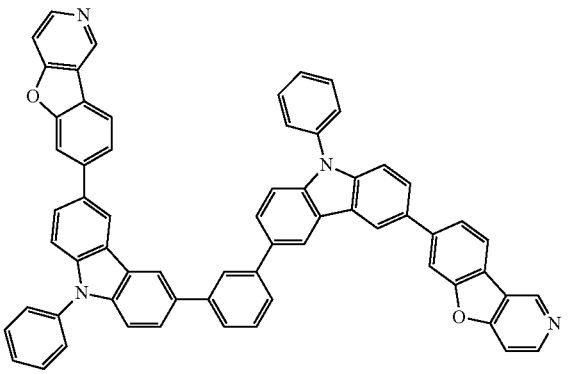 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 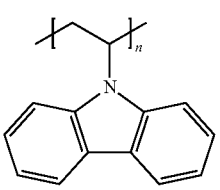 | Appl. Phys. Lett. 77, 2280 (2000) |

TABLE 4-continued

| MATERIAL | EXAMPLES OF MATERIAL | PUBLICATIONS |
|---|---|---|
| Spirofluorene compounds | | WO2004093207 |
| Metal phenoxy-benzooxazole compounds | | WO2005089025 |
| | | WO2006132173 |
| | | JP200511610 |
| Spirofluorene-carbazole compounds | | JP2007254297 |

TABLE 4-continued
| MATERIAL | EXAMPLES OF MATERIAL | PUBLICATIONS |
|---|---|---|
| | 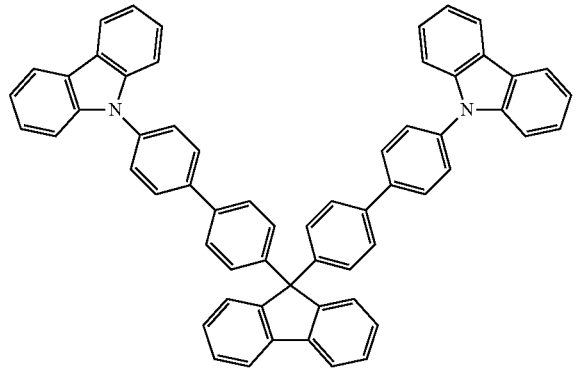 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 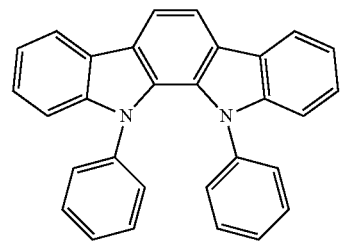 [SMILES: c1ccc(-n2c3ccccc3c3ccc4c5ccccc5n(-c5ccccc5)c4c32)cc1] | WO2007063796 |
| | 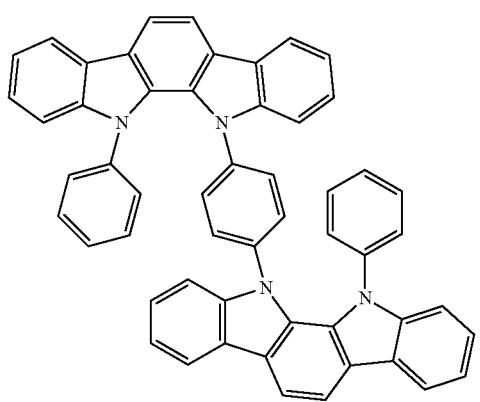 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 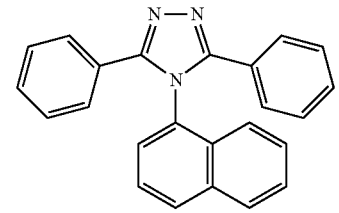 [SMILES: c1ccc(-c2nnc(-c3ccccc3)n2-c2cccc3ccccc23)cc1] | J. Appl. Phys. 90, 5048 (2001) |
| | 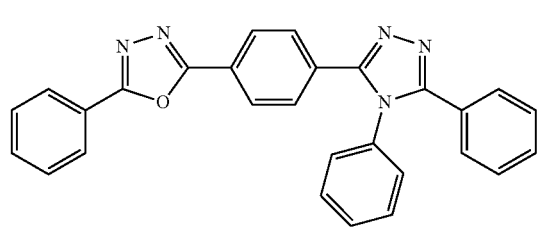 [SMILES: c1ccc(-c2nnc(-c3ccc(-c4nnc(-c5ccccc5)n4-c4ccccc4)cc3)o2)cc1] | WO2004107822 |

TABLE 4-continued
| MATERIAL | EXAMPLES OF MATERIAL | PUBLICATIONS |
|---|---|---|
| Tetraphenylene complexes | 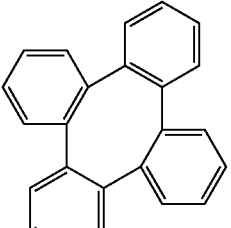 | US20050112407 |
| Metal phenoxypyridine compounds | 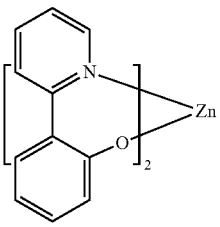 | WO2005030900 |
| Metal coordination complexes (e.g., Zn, A with NN ligands) | 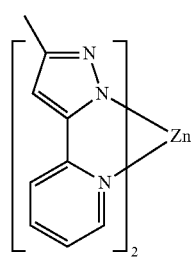 | US20040137268, US20040137267 |
| Blue hosts | | |
| Arylcarbazoles | 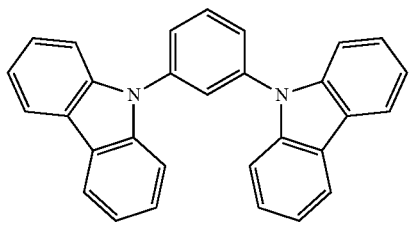 [SMILES: c1cc(-n2c3ccccc3c3ccccc32)cc(-n2c3ccccc3c3ccccc32)c1] | Appl. Phys. Lett, 82, 2422 (2003) |
| | 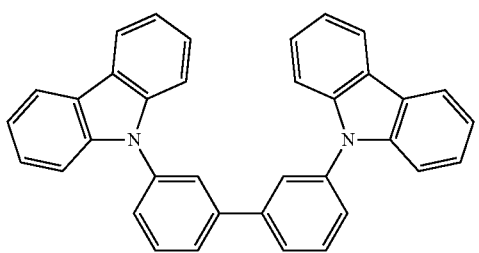 [SMILES: c1cc(-c2cccc(-n3c4ccccc4c4ccccc43)c2)cc(-n2c3ccccc3c3ccccc32)c1] | US20070190359 |

TABLE 4-continued
| MATERIAL | EXAMPLES OF MATERIAL | PUBLICATIONS |
|---|---|---|
| Dibenzothiophene/ Dibenzofuran- carbazole compounds | 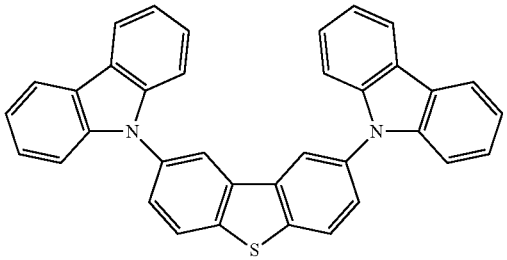 [SMILES: c1ccc2c(c1)c1ccccc1n2-c1ccc2sc3ccc(-n4c5ccccc5c5ccccc54)cc3c2c1] | WO2006114966, US20090167162 |
| | 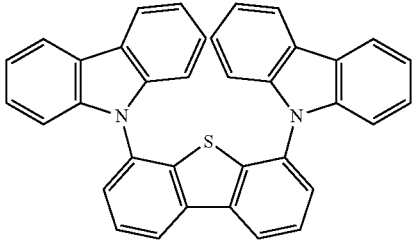 [SMILES: c1cc(-n2c3ccccc3c3ccccc32)c2sc3c(-n4c5ccccc5c5ccccc54)cccc3c2c1] | US20090167162 |
| | 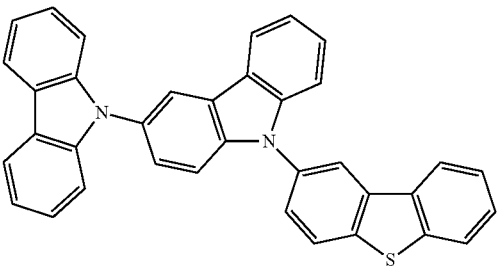 [SMILES: c1ccc2c(c1)sc1ccc(-n3c4ccccc4c4cc(-n5c6ccccc6c6ccccc65)ccc43)cc12] | WO2009086028 |
| | 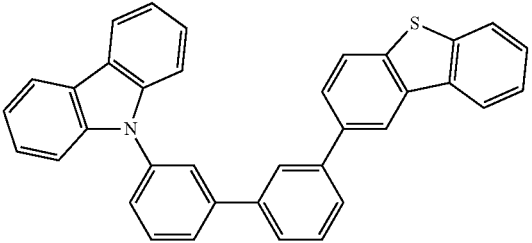 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 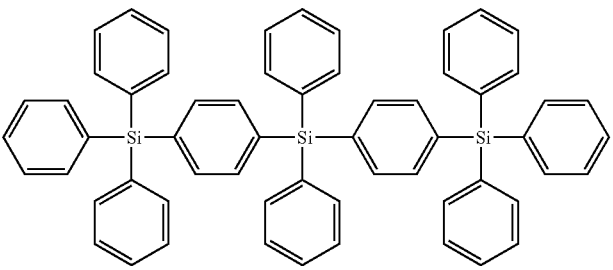 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 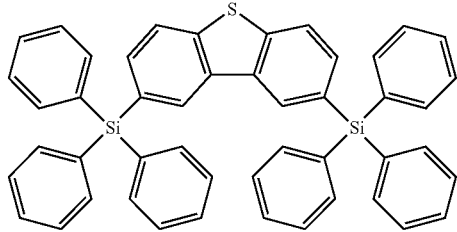 | WO2009003898 |

TABLE 4-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | U.S. Pat. No. 7154114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE 4-continued
| MATERIAL | EXAMPLES OF MATERIAL | PUBLICATIONS |
|---|---|---|
| | 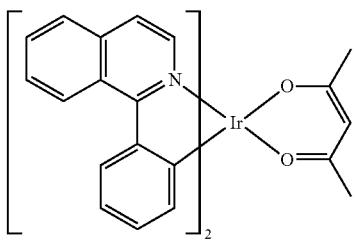 | US2006835469 |
| | 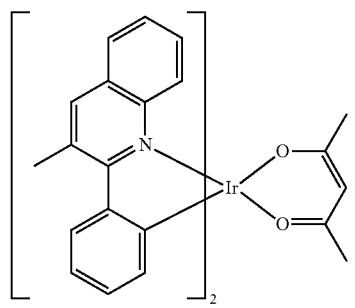 | US2006835469 |
| | 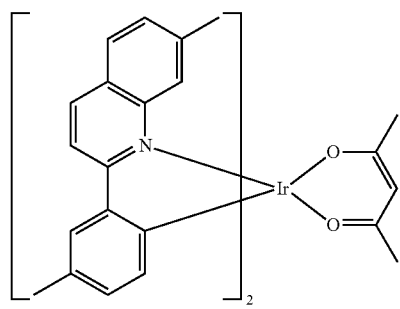 | US20060202194 |
| | 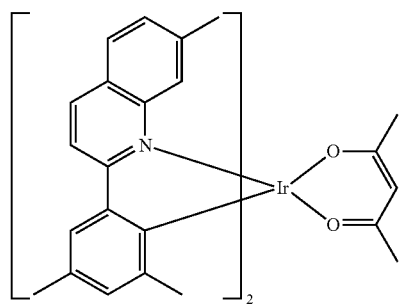 | US20060202194 |
| | 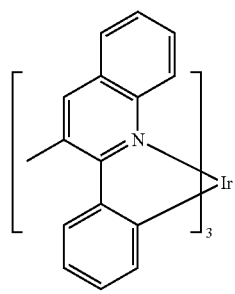 | US20070087321 |

TABLE 4-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 4-continued

| MATERIAL | EXAMPLES OF MATERIAL | PUBLICATIONS |
|---|---|---|
| Osminum(III) complexes | [structure: Os(PPhMe$_2$)$_2$ complex with CF$_3$-pyrazolyl-pyridine ligand]$_2$ | Chem. Mater. 17, 3532 (2005) |
| Ruthenium(II) complexes | [structure: Ru(PPhMe$_2$)$_2$ complex with tBu-pyrazolyl-isoquinoline ligand]$_2$ | Adv. Mater. 17, 1059 (2005) |
| Rhenium (I), (II), and (III) complexes | [structure: Re(CO)$_4$ complex with 8-hydroxyquinoline ligand] | US20050244673 |

Green dopants

| MATERIAL | EXAMPLES OF MATERIAL | PUBLICATIONS |
|---|---|---|
| Iridium(III) organometallic complexes | [structure: Ir(ppy)$_3$] and its derivatives | Inorg. Chem. 40, 1704 (2001) |
| | [structure: Ir(ppy)$_2$(acac)] | US20020034656 |

TABLE 4-continued

| MATERIAL | EXAMPLES OF MATERIAL | PUBLICATIONS |
|---|---|---|
|  |  | U.S. Pat. No. 7,332,232 |
|  |  | US20090108737 |
|  |  | US20090039776 |
|  |  | U.S. Pat. No. 6,921,915 |

TABLE 4-continued

| MATERIAL | EXAMPLES OF MATERIAL | PUBLICATIONS |
| --- | --- | --- |
| | [structure] | U.S. Pat. No. 6,687,266 |
| | [structure] | Chem. Mater. 16, 2480 (2004) |
| | [structure] | US20070190359 |
| | [structure] | US 20060008670 JP2007123392 |
| | [structure] | Adv. Mater. 16, 2003 (2004) |

TABLE 4-continued
| MATERIAL | EXAMPLES OF MATERIAL | PUBLICATIONS |
|---|---|---|
| | 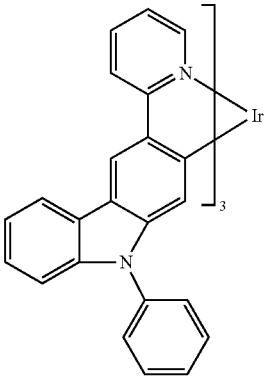 | Angew. Chem. int. Ed. 2006, 45, 7800 |
| | 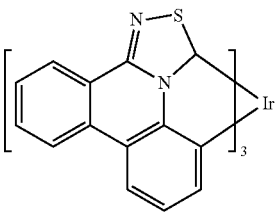 | WO2009050290 |
| | 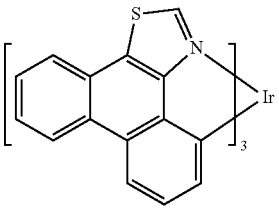 | US20090165846 |
| | 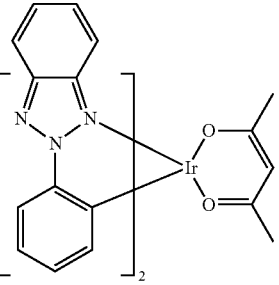 | US20080015355 |
| Monomer for polymeric metal organometallic compounds | 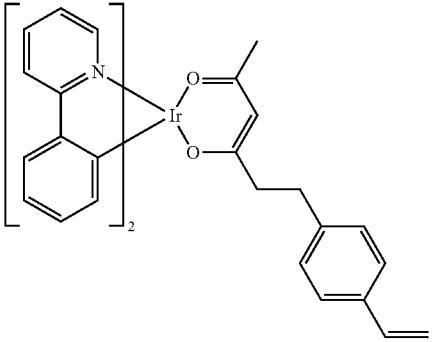 | U.S. Pat. No. 7,250,226, U.S. Pat No. 7,396,598 |

TABLE 4-continued
| MATERIAL | EXAMPLES OF MATERIAL | PUBLICATIONS |
|---|---|---|
| Pt(II) organometallic complexes, including polydentated ligands | 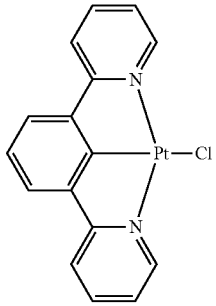 | Appl. Phys. Lett. 86, 153505 (2005) |
| | 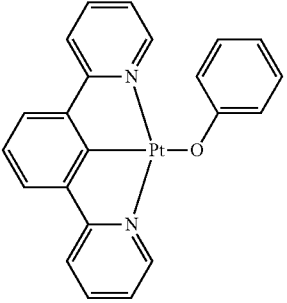 | Appl. Phys. Lett. 86, 153505(2005) |
| | 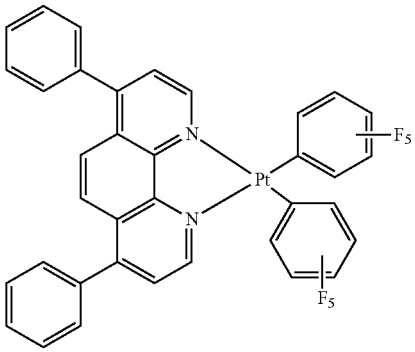 | Chem. Lett. 34, 592 (2005) |
| | 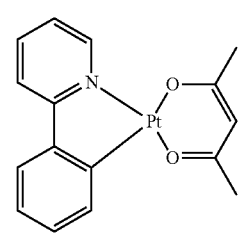 | WO2002015645 |
| | 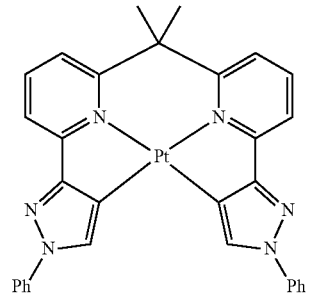 | US20060263635 |

TABLE 4-continued
| MATERIAL | EXAMPLES OF MATERIAL | PUBLICATIONS |
|---|---|---|
| Cu complexes | 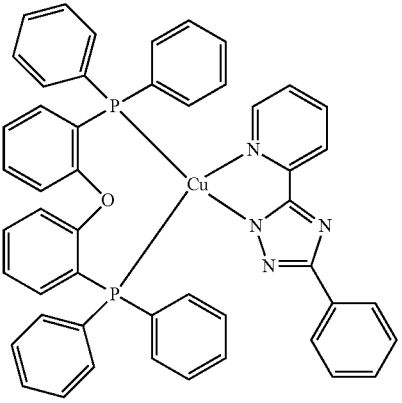 | WO2009000673 |
| Gold complexes | 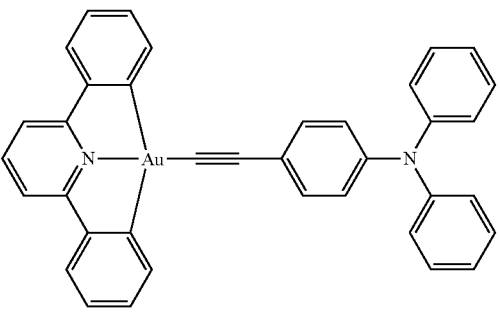 | Chem. Commun. 2906 (2005) |
| Rhenium(III) complexes | 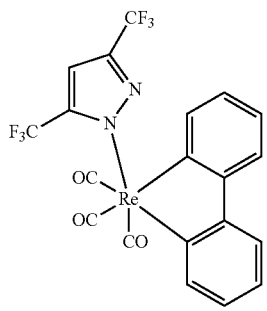 | Inorg. Chem. 42, 1248 (2003) |
| Deuterated organometallic complexes | 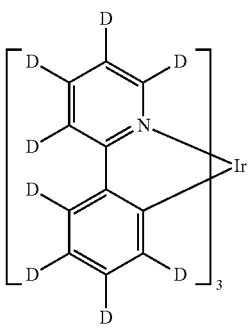 | US20030138657 |

TABLE 4-continued

| MATERIAL | EXAMPLES OF MATERIAL | PUBLICATIONS |
|---|---|---|
| Organometallic complexes with two or more metal centers | | US20030152802 |

| | | U.S. Pat. No. 7,090,928 |

Blue dopants

| Iridium(III) organometallic complexes | | WO2002002714 |

| | | WO2006009024 |

TABLE 4-continued

| MATERIAL | EXAMPLES OF MATERIAL | PUBLICATIONS |
|---|---|---|
| | | US20060251923 |
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |
| | | U.S. Pat. No. 7,338,722 |

| MATERIAL | EXAMPLES OF MATERIAL | PUBLICATIONS |
|---|---|---|
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |

TABLE 4-continued
| MATERIAL | EXAMPLES OF MATERIAL | PUBLICATIONS |
|---|---|---|
| | 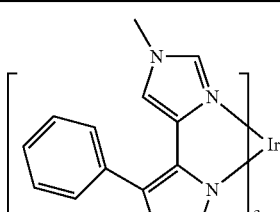 | WO2007004380 |
| | 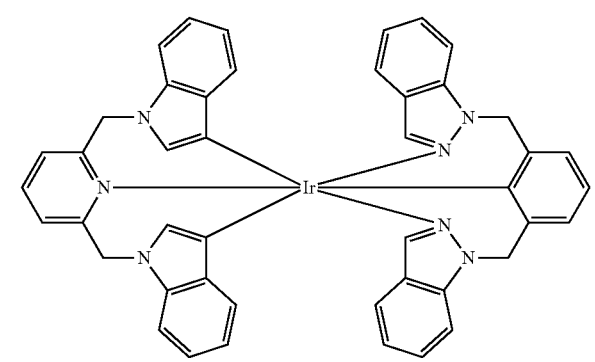 | WO2006082742 |
| Osmium(II) complexes | 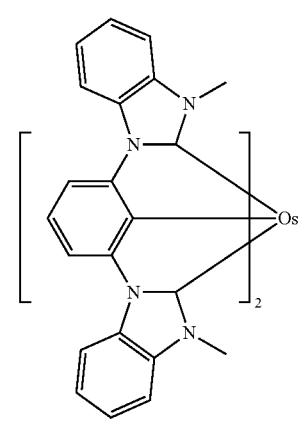 | U.S. pat. No. 7,279,704 |
| | 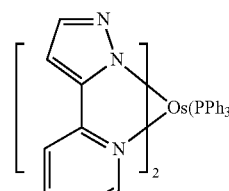 | Organometallics 23, 3745 (2004) |
| Gold complexes | 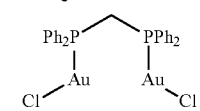 | Appl. Phys. Lett.74,1361 (1999) |
| Platinum(II) complexes | 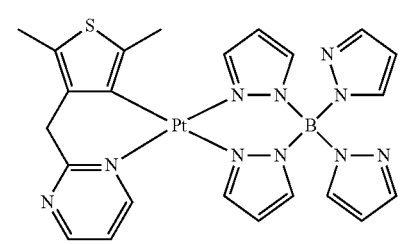 | WO2006098120, WO2006103874 |

TABLE 4-continued
| MATERIAL | EXAMPLES OF MATERIAL | PUBLICATIONS |
|---|---|---|
| | Exciton/hole blocking layer materials | |
| Bathocuprine compounds (e.g., BCP, BPhen) | 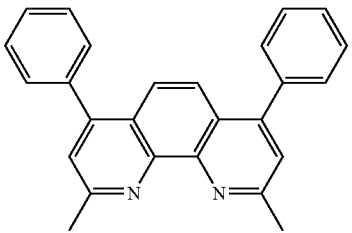 [SMILES: Cc1cc(-c2ccccc2)c2ccc3c(-c4ccccc4)cc(C)nc3c2n1] | Appl. Phys. Lett. 75. 4 (1999) |
| | | Appl. Phys. Lett. 79, 449 (2001) |
| Metal 8-hydroxyquinolates (e.g., BAlq) | 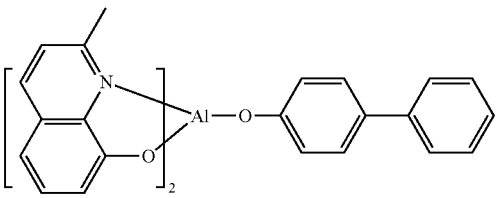 | Appl. Phys. Lett. 81, 162 (2002) |
| 5-member ring electron deficient heterocycles such as triazole, oxadiazole, imidazole, benzoimidazole | 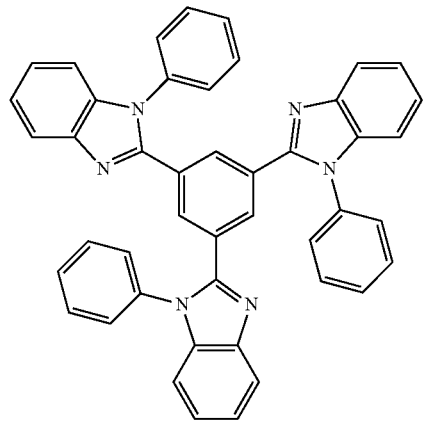 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 4-continued

| MATERIAL | EXAMPLES OF MATERIAL | PUBLICATIONS |
|---|---|---|
| Triphenylene compounds | | US20050025993 |
| Fluorinated aromatic compounds | | Appl. Phys. Lett. 79, 156(2001) |
| Phenothiazine-S-oxide | | WO2008132085 |

TABLE 4-continued
| MATERIAL | EXAMPLES OF MATERIAL | PUBLICATIONS |
|---|---|---|
| Electron transporting materials | | |
| Anthracene-benzoimidazole compounds | 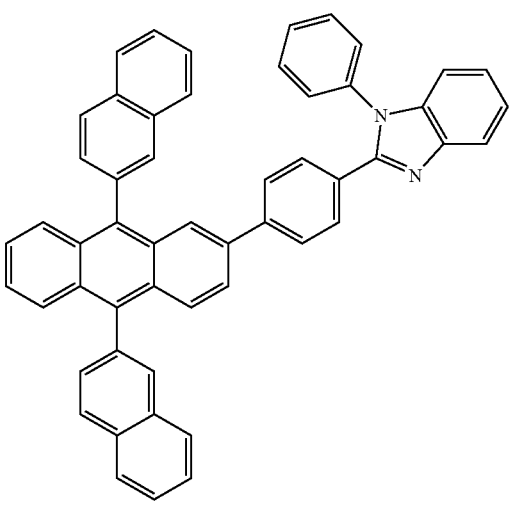 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 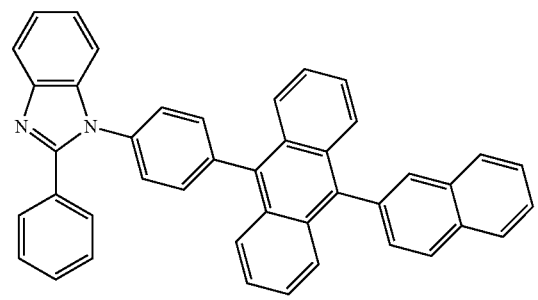 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 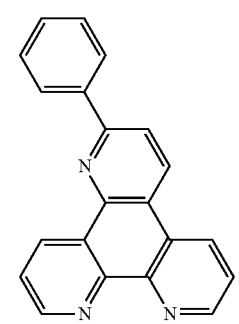 [SMILES: c1ccc(-c2ccc3c4cccnc4c4ncccc4c3n2)cc1] | US20090115316 |
| Anthracene-benzothiazole compounds | 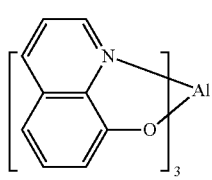 | Appl. Phys. Lett. 89, 063504 (2006) |
| Metal 8-hydroxyquinolates (e.g., Alq$_3$, Zrq$_4$) | | Appl. Phys. Lett. 51, 913(1987) U.S. Pat. No. 7,230,107 |

TABLE 4-continued

| MATERIAL | EXAMPLES OF MATERIAL | PUBLICATIONS |
| --- | --- | --- |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett, 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 4-continued

| MATERIAL | EXAMPLES OF MATERIAL | PUBLICATIONS |
| --- | --- | --- |
| Silole compounds | | Org. Electron. 4, 113 (2003) |
| Arylborane compounds | | J. Am. Chem. Soc. 120, 9714(1998) |
| Fluorinated aromatic compounds | | J. Am. Chem. Soc. 122, 1832 (2000) |
| Fullerene (e.g., C60) | | US20090101870 |
| Triazine complexes | | US20040036077 |

TABLE 4-continued

| MATERIAL | EXAMPLES OF MATERIAL | PUBLICATIONS |
|---|---|---|
| Zn (N^N) complexes | | U.S. Pat. No. 6,528,187 |

Experimental

Chemical abbreviations used throughout this document are as follows: dba is dibenzylideneacetone, EtOAc is ethyl acetate, dppf is 1,1'-bis(diphenylphosphino)ferrocene, DCM is dichloromethane, SPhos is dicyclohexyl(2',6'-dimethoxy-[1,1'-biphenyl]-3-yl)phosphine, THF is tetrahydrofuran.

Synthesis of Compound 1

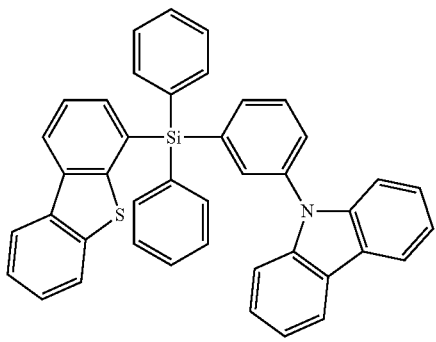

Compound 1

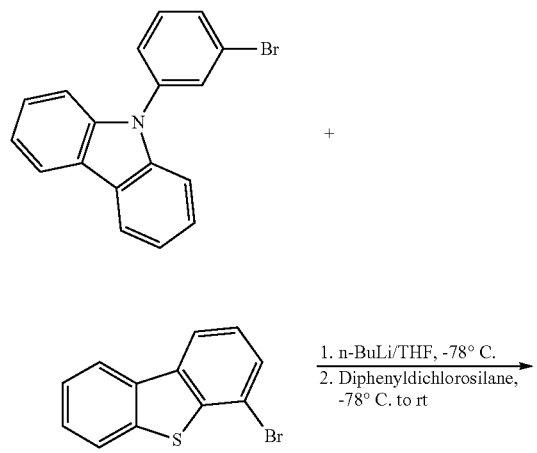

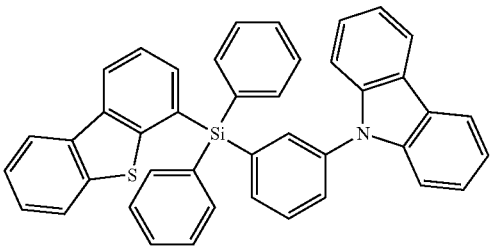

Into a solution of 9-(3-bromophenyl)-9H-carbazole (5 g, 15.52 mmol) and 4-bromodibenzo[b,d]thiophene (4.08 g, 15.52 mmol) in 100 mL of THF was added n-butyllithium solution in hexane (2.5 M, 21.34 mL, 34.1 mmol) dropwise at −78° C., and stirred for 1 h. Diphenyldichlorosilane (3.19 mL, 15.52 mmol) was dissolved in THF (10 mL) and added dropwise into the lithiated mixture. The mixture was allowed to warm to room temperature overnight, quenched with water and NH₄Cl solution, extracted with EtOAc, dried over Na₂SO₄ and filtered. Upon evaporation of the solvent, the solid was recrystallized from DCM to yield Compound 1 as a white solid (3.4 g, 36%).

Synthesis of Compound 2

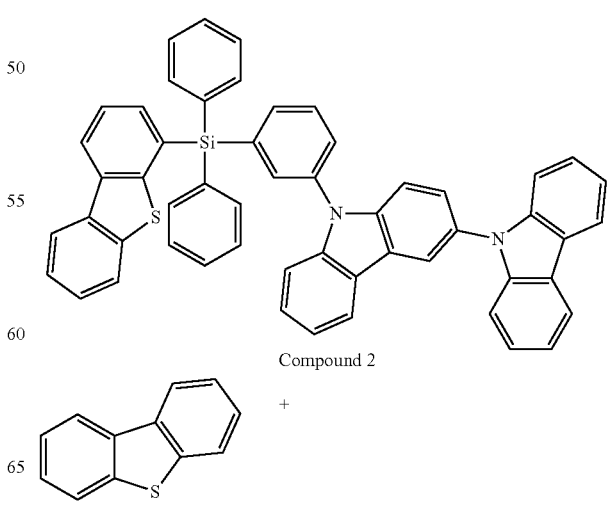

Compound 2

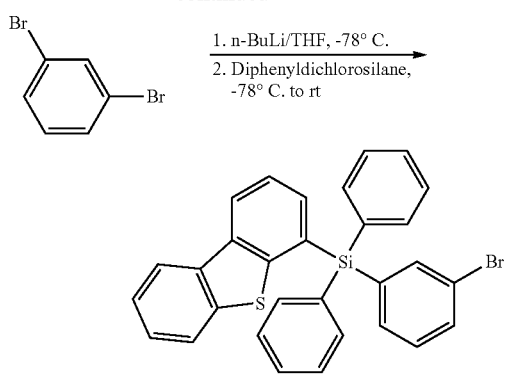

Into a solution of dibenzo[b,d]thiophene (4.80 g, 26.1 mmol) in ether (70 mL) was added n-butyllithium solution in hexane (2.5 M, 9.48 mL, 23.70 mmol) dropwise at −78° C., and the solution was allowed to warm to room temperature and then heated at 35° C. oil bath for 2 h to yield a red solution of dibenzo[b,d]thiophen-4-yl lithium.

In another flask was prepared a solution of m-bromophenyl lithium by addition of n-butyllithium solution in hexane (2.5 M, 9.48 mL, 23.70 mmol) into a solution of 1,3-dibromobenzene (2.56 mL, 21.20 mmol) in ether (70 mL) at −78° C. followed by stirring at this temperature for 3.5 h. This m-bromophenyl lithium solution was added dropwise into a solution of dichlorodiphenylsilane (4.88 mL, 23.70 mmol) in ether (70 mL) at −78° C. The resultant reaction solution was stirred at this temperature for 2 h before the dibenzo[b,d]thiophen-4-yl lithium solution prepared above was introduced dropwise. The resultant solution was allowed to slowly warm to room temperature overnight. It was quenched with water, extracted with ether and dried over $Na_2SO_4$. Upon evaporation of the solvent, the residue was purified by column chromatography on silica gel with hexane/DCM (9/1, v/v) as eluent to yield (3-bromophenyl)(dibenzo[b,d]thiophen-4-yl)diphenylsilane as a white powder (3.84 g, 31%).

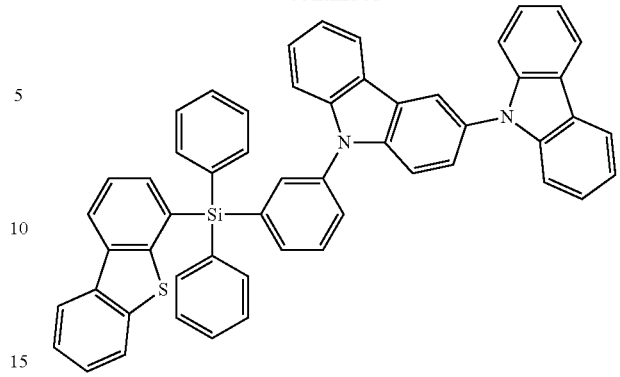

A mixture of (3-bromophenyl)(dibenzo[b,d]thiophen-4-yl)diphenylsilane (3.4 g, 6.52 mmol), 9H-3,9'-bicarbazole (2.4 g, 7.17 mmol), $Pd_2(dba)_3$ (0.119 g, 0.130 mmol), SPhos (0.107 g, 0.261 mmol), and sodium tert-butoxide (1.253 g, 13.04 mmol) in m-xylene (50 mL) was heated at 140° C. under $N_2$ overnight. After cooling to room temperature, it was passed through a short plug of Celite®, and washed with toluene and DCM. The combined organic solution was evaporated, and the residue was purified by column chromatography on silica gel with hexane/DCM (7.5/2.5, v/v) as eluent to yield Compound 2 (4.2 g, 83%) as a white powder.

Synthesis of Compound 3

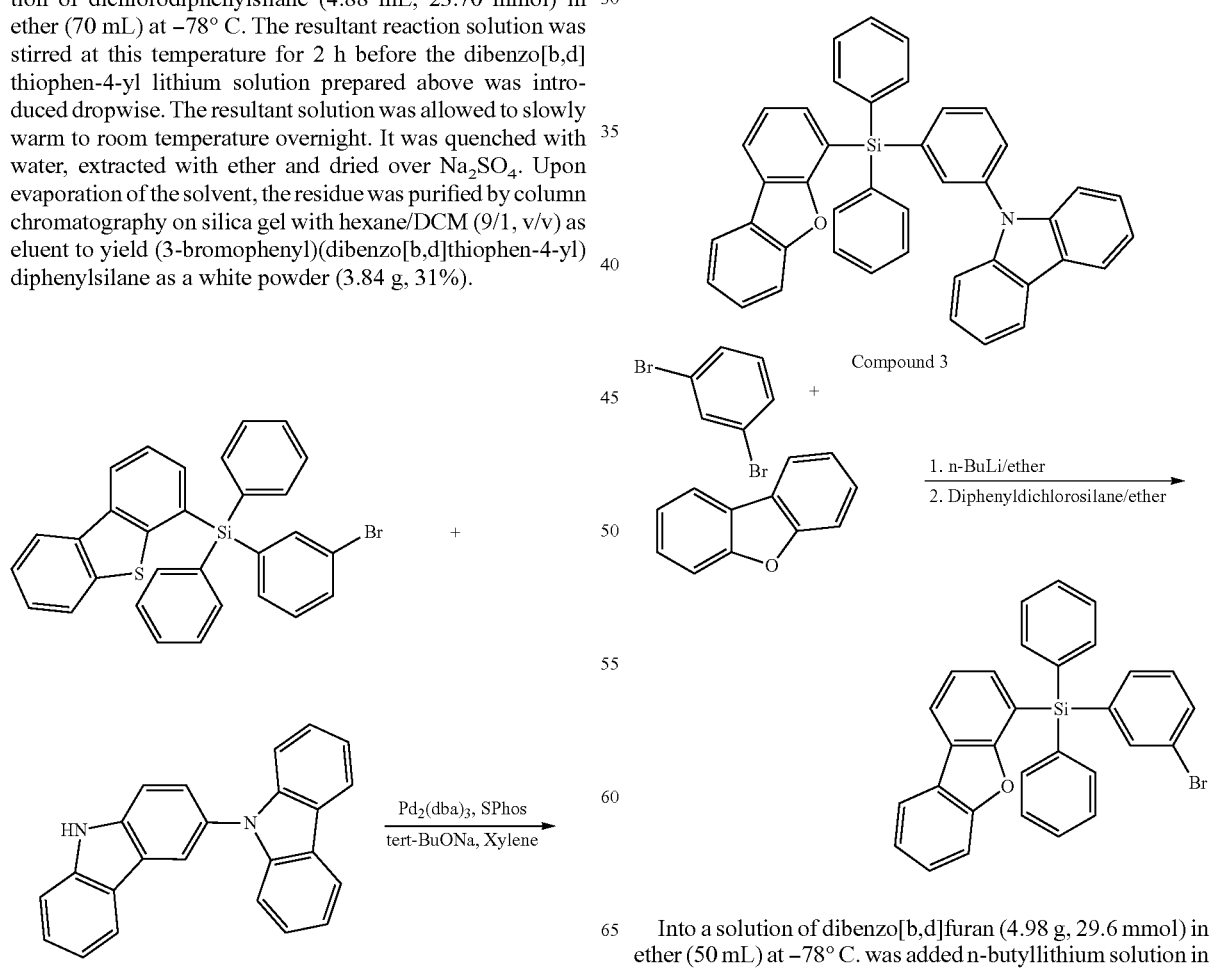

Into a solution of dibenzo[b,d]furan (4.98 g, 29.6 mmol) in ether (50 mL) at −78° C. was added n-butyllithium solution in hexane (2.5 M, 9.48 mL, 23.70 mmol) dropwise and the solution was allowed to warm to room temperature and stirred for 20 h to yield a dibenzo[b,d]furan-4-yl lithium solution. Into a solution of 1,3-dibromobenzene (2.56 mL, 21.20 mmol) in ether (50 mL) was added n-butyllithium solution in hexane (2.5 M, 9.48 mL, 23.70 mmol) dropwise at −78° C. The reaction solution was stirred at this temperature for 3.5 h before adding into a solution of dichlorodiphenylsilane (4.88 mL, 23.70 mmol) in ether (50.0 mL) at −78° C. The resultant reaction solution was stirred at this temperature for 2 h before the dibenzo[b,d]furan-4-yl lithium solution prepared above was introduced dropwise. The reaction mixture was allowed to slowly warm to room temperature overnight at which time it was quenched with water, extracted with ether, and dried over Na$_2$SO$_4$. Upon filtration and evaporation of the solvent, the residue was purified by column chromatography on silica gel with hexane/DCM (9/1, v/v) as eluent to yield (3-bromophenyl)(dibenzo[b,d]furan-4-yl)diphenylsilane (6.2 g, 52%) as a white powder.

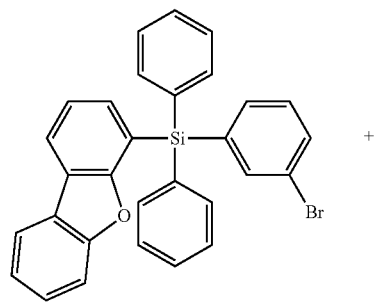

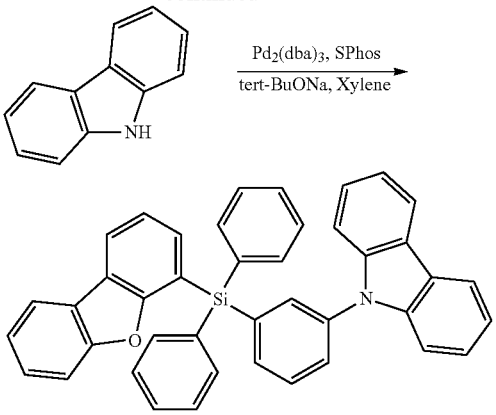

A suspension of (3-bromophenyl)(dibenzo[b,d]furan-4-yl)diphenylsilane (3 g, 5.93 mmol), 9H-carbazole (0.992 g, 5.93 mmol), Pd$_2$(dba)$_3$ (0.109 g, 0.119 mmol), SPhos (0.097 g, 0.237 mmol) and sodium tert-butoxide (1.1 g, 11.87 mmol) in m-xylene (50 mL) was refluxed at 140° C. under nitrogen overnight. After cooling to room temperature, it was passed through a short plug of Celite®, and washed with toluene and DCM. The combined solution was evaporated, and the residue was purified by column chromatography on silica gel with hexane/DCM (7.5/2.5, v/v) as eluent and precipitation from DCM to methanol to yield Compound 3 as a while powder (3.2 g, 91%).

Synthesis of Compound 4

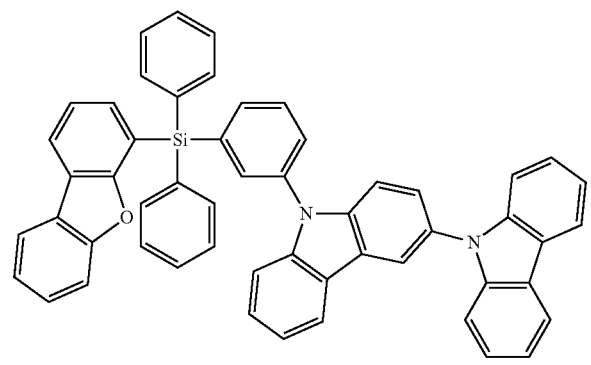

Compound 4

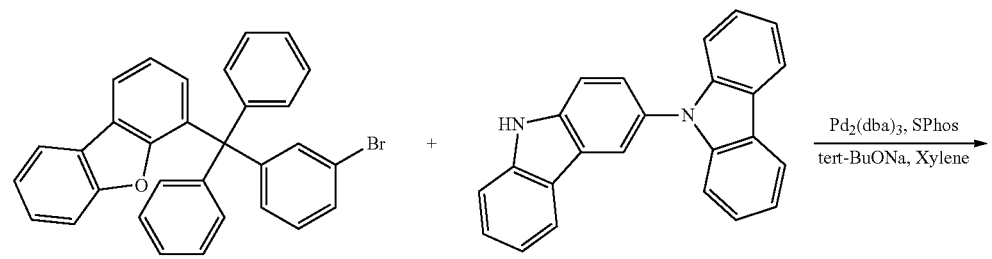

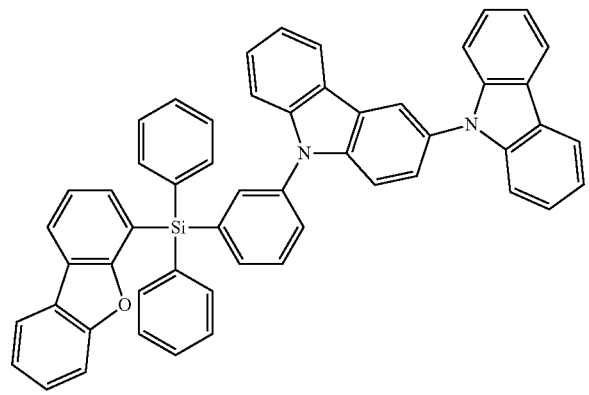

A suspension of (3-bromophenyl)(dibenzo[b,d]furan-4-yl)diphenylsilane (2.75 g, 5.44 mmol), 9H-3,9'-bicarbazole (1.81 g, 5.44 mmol), Pd$_2$(dba)$_3$ (0.10 g, 0.10 mmol), SPhos (0.089 g, 0.22 mmol), and sodium tert-butoxide (1.05 g, 10.88 mmol) in m-xylene (50 mL) was heated at 140° C. overnight. After cooling to room temperature, it was passed through a short plug of Celite®, and washed with toluene and DCM. The combined solution was evaporated, and the residue was purified by column chromatography on silica gel with hexane/DCM (8/2, v/v) as eluent to yield Compound 4 (3.5 g, 85%) as a white powder.

A mixture solution of 1-(3-bromo-9H-carbazol-9-yl)ethanone (13.80 g, 47.9 mmol), 4,4,4',4',5,5,5',5'-octamethyl-2,2'-bi(1,3,2-dioxaborolane) (14.59 g, 57.5 mmol), potassium acetate (9.40 g, 96 mmol), dppf (0.585 g, 0.958 mmol) and Pd$_2$(dba)$_3$ (0.877 g, 0.958 mmol) in dioxane (300 mL) was refluxed under N$_2$ overnight. After cooling to room temperature, it was diluted with water (250 mL) and extracted with EtOAc (3×70 mL). The organic phase was isolated and dried over Na$_2$SO$_4$. Upon evaporation off the solvent, the residue was purified by column chromatography on silica with hexane/EtOAc (9/1, v/v) as eluent, and recrystallized from the same solvent to yield 1-(3-(4,4,5,5-tetramethyl-1,3,2-dioxaborolan-2-yl)-9H-carbazol-9-yl)ethanone (10.5 g, 65%) as white crystals.

Synthesis of Compound 5

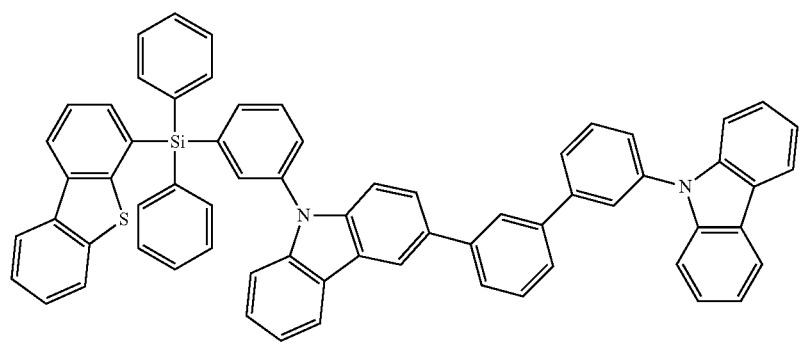

Compound 5

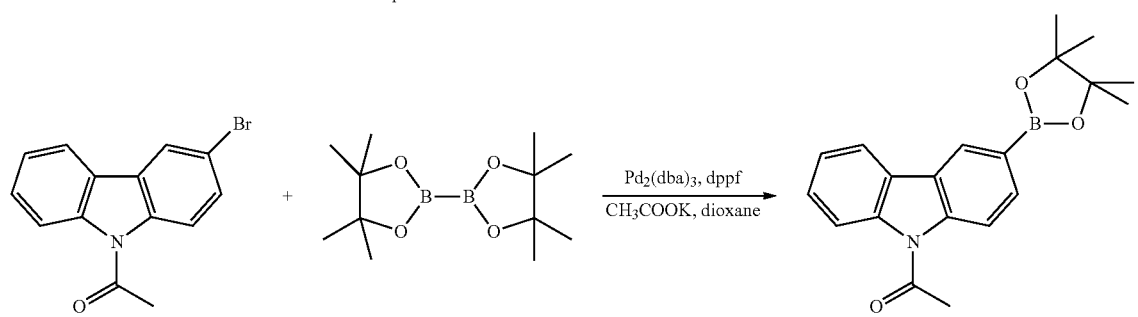

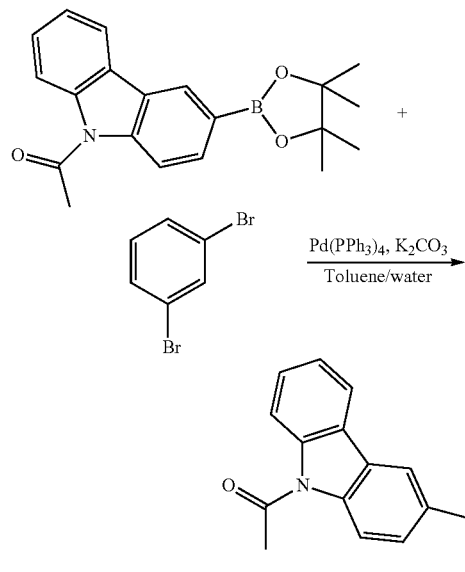

+

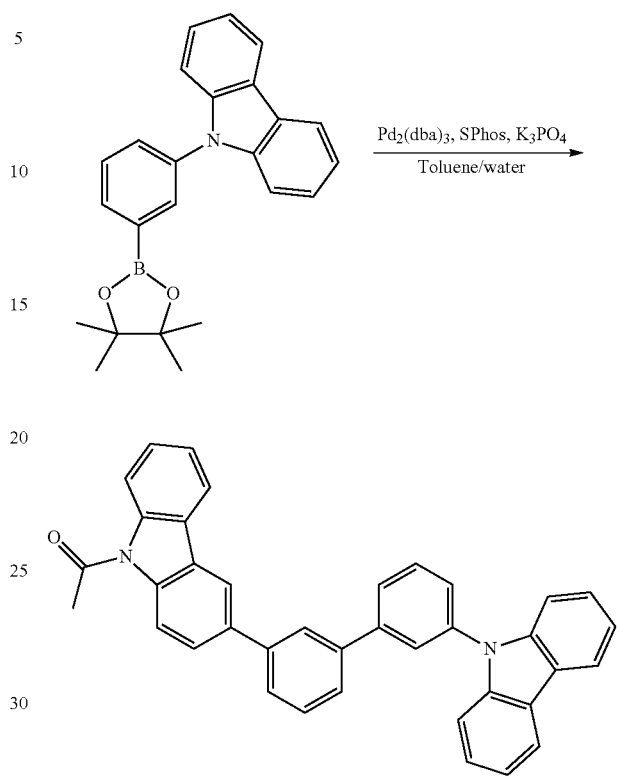

A mixture solution of 1-(3-(4,4,5,5-tetramethyl-1,3,2-dioxaborolan-2-yl)-9H-carbazol-9-yl)ethanone (10.00 g, 29.8 mmol), 1,3-dibromobenzene (17.59 g, 74.6 mmol), Pd(PPh$_3$)$_4$ (0.689 g, 0.597 mmol) and K$_2$CO$_3$ (12.37 g, 89 mmol) in toluene (100 mL) and water (20 mL) was refluxed under N$_2$ overnight. After cooling to room temperature, the organic phase was isolated and the solvent was evaporated. The residue was purified by column chromatography on silica gel with hexane/DCM (1/1, v/v) as eluent to yield 1-(3-(3-bromophenyl)-9H-carbazol-9-yl)ethanone (2.5 g, 23%) as a white solid.

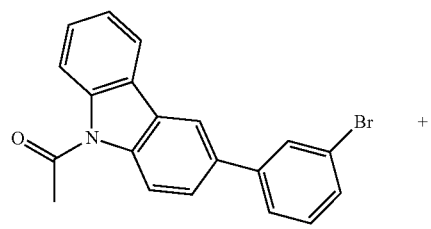 +

A mixture solution of 1-(3-(3-bromophenyl)-9H-carbazol-9-yl)ethanone (2.50 g, 6.86 mmol), 9-(3-(4,4,5,5-tetramethyl-1,3,2-dioxaborolan-2-yl)phenyl)-9H-carbazole (2.53 g, 6.86 mmol), Pd$_2$(dba)$_3$ (0.063 g, 0.069 mmol), (SPhos) (0.056 g, 0.137 mmol) and K$_3$PO$_4$ (4.74 g, 20.59 mmol) in toluene (180 mL) and water (5 mL) was refluxed under N$_2$ overnight. After cooling to room temperature, the organic solution was isolated. Upon evaporation of the solvent, the residue was purified by column chromatography on silica gel with hexane/DCM (1/1 to 1/4, v/v) as eluent to yield 1-(3-(3'-(9H-carbazol-9-yl)-[1,1'-biphenyl]-3-yl)-9H-carbazol-9-yl)ethanone (3.2 g, 89%) as a white solid.

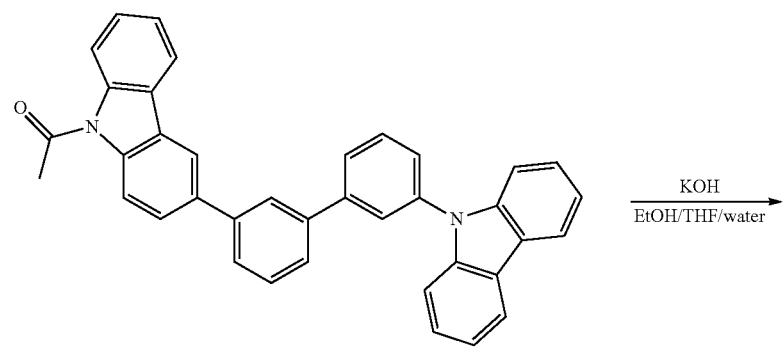

KOH
———————→
EtOH/THF/water

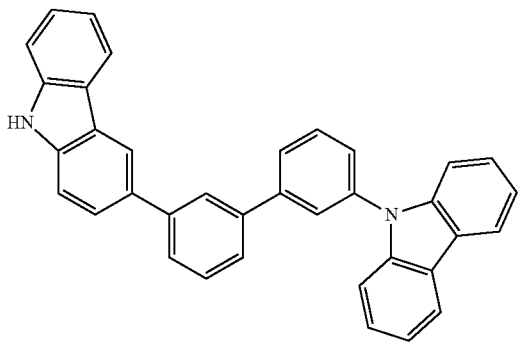

A mixture solution of 1-(3-(3'-(9H-carbazol-9-yl)-[1,1'-biphenyl]-3-yl)-9H-carbazol-9-yl)ethanone (3.30 g, 6.27 mmol) and KOH (3.5 g, 62.7 mmol) in THF (50 mL), water (50 mL) and ethanol (50 mL) was refluxed for 1 h. After cooling to room temperature, it was diluted with water and extracted with EtOAc (4×50 mL). The organic fractions were combined, dried over $Na_2SO_4$ and concentrated to induce the precipitation of 3-(3'-(9H-carbazol-9-yl)-[1,1'-biphenyl]-3-yl)-9H-carbazole (2.6 g, 86%) as a white solid.

5.57 mmol), sodium tert-butoxide (1.071 g, 11.14 mmol), $Pd_2(dba)_3$ (0.102 g, 0.111 mmol) and SPhos (0.091 g, 0.223 mmol) in xylene (150 mL) was refluxed under $N_2$ for 18 h. After cooling to room temperature, an aqueous solution (100 mL) of 10% $NaHSO_3$ was added and stirred for 1 h. The organic phase was isolated and dried over $Na_2SO_4$. Upon evaporation off the solvent, the residue was purified by col-

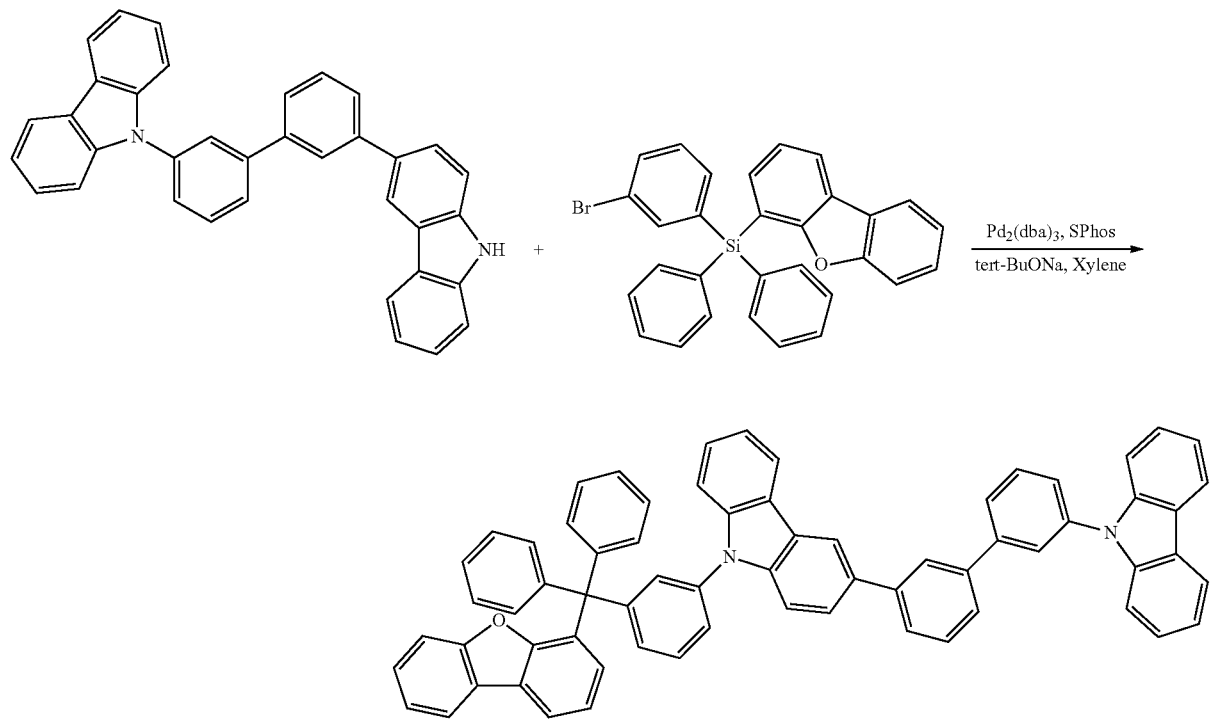

A mixture solution of 3-(3'-(9H-carbazol-9-yl)-[1,1'-biphenyl]-3-yl)-9H-carbazole (2.70 g, 5.57 mmol), (3-bromophenyl)(dibenzo[b,d]furan-4-yl)diphenylsilane (2.82 g, umn chromatography on silica gel with hexane/DCM (7/3, v/v) as eluent to yield Compound 5 (3.3 g, 65%) as a white powder.

Synthesis of Compound 6

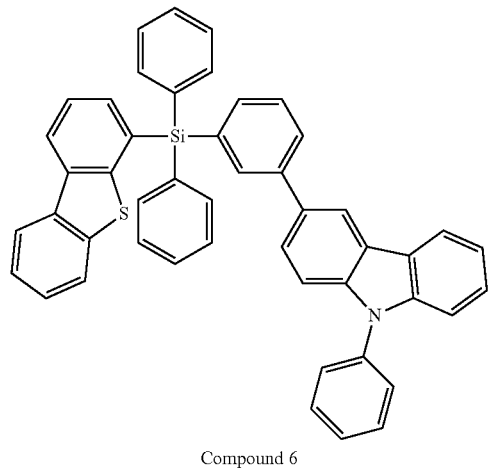

Compound 6

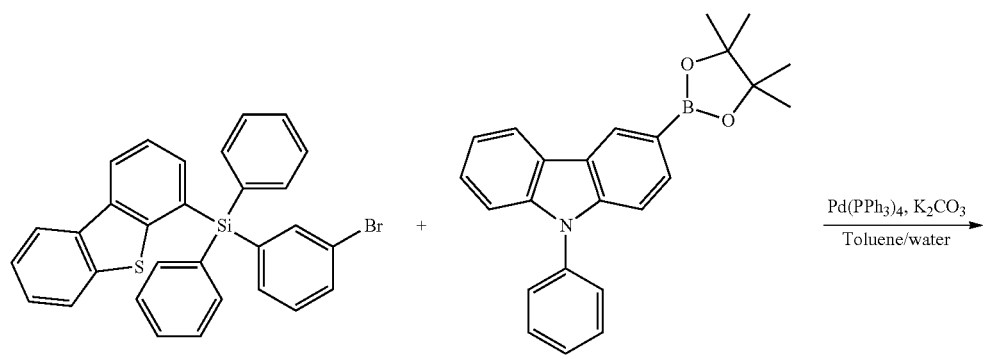

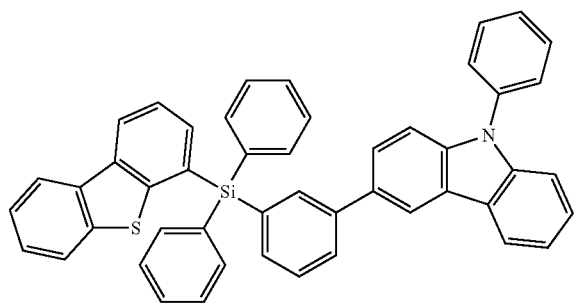

A mixture solution of (3-bromophenyl)(dibenzo[b,d]thiophen-4-yl)diphenylsilane (3.50 g, 6.71 mmol), 9-phenyl-3-(4,4,5,5-tetramethyl-1,3,2-dioxaborolan-2-yl)-9H-carbazole (2.478 g, 6.71 mmol), $K_2CO_3$ (1.9 g, 13.42 mmol) and $Pd(PPh_3)_4$ (0.155 g, 0.134 mmol) in toluene (150 mL) and water (50 mL) was refluxed under $N_2$ overnight. After cooling to room temperature, the organic phase was isolated. Upon evaporation of the solvent, the residue was purified by column chromatography on silica gel with hexane/DCM (4/1, v/v) as eluent to yield Compound 6 (3.3 g, 72%) as a white solid.

Synthesis of Compound 7

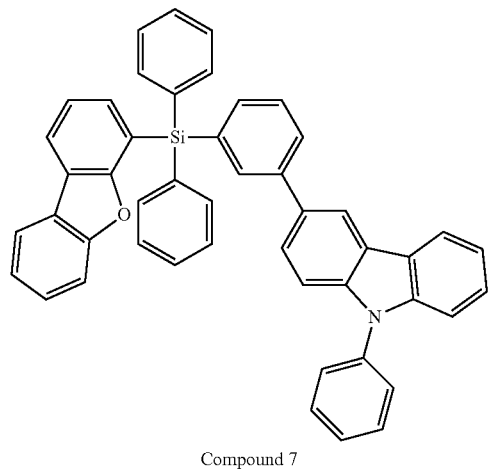

Compound 7

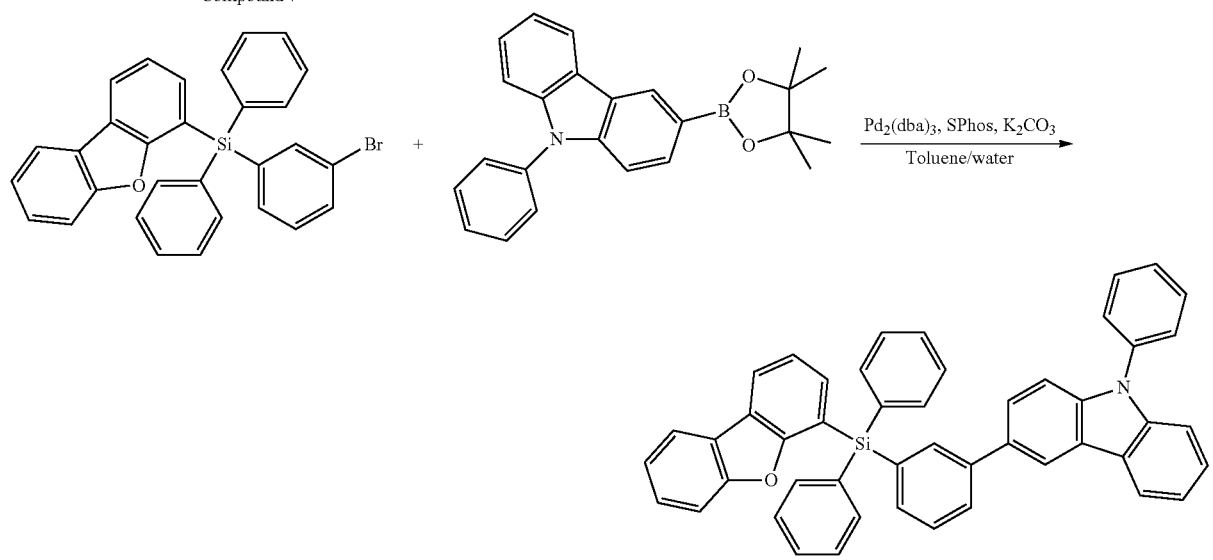

A mixture of (3-bromophenyl)(dibenzo[b,d]furan-4-yl)diphenylsilane (3.5 g, 6.92 mmol), 9-phenyl-3-(4,4,5,5-tetramethyl-1,3,2-dioxaborolan-2-yl)-9H-carbazole (2.56 g, 6.92 mmol), $Pd_2(dba)_3$ (0.127 g, 0.138 mmol), SPhos (0.114 g, 0.277 mmol) and $K_2CO_3$ (2.87 g, 20.77 mmol) in toluene (30 mL) and water (10 mL) was heated at 100° C. overnight. After cooling to room temperature, the organic phase was isolated. Upon evaporation of the solvent, the residue was purified by column chromatography on silica gel with hexane/DCM (9/1, v/v) as eluent to yield Compound 7 (3.3 g, 72%) as a white solid.

Synthesis of Compound 10

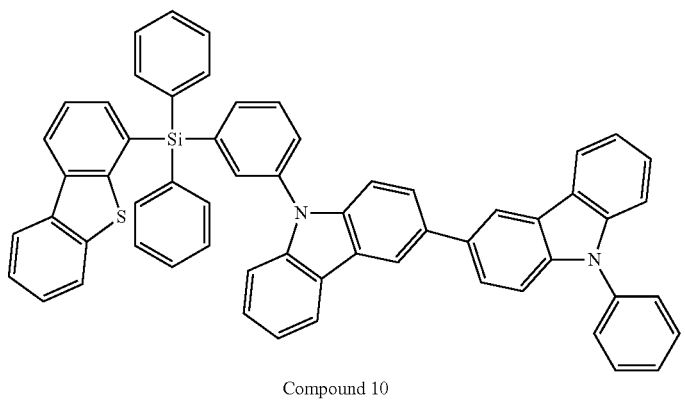

Compound 10

-continued

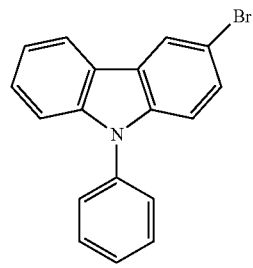 + 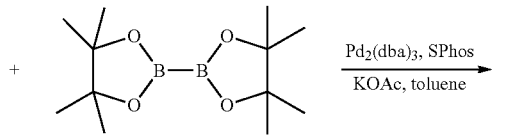 → 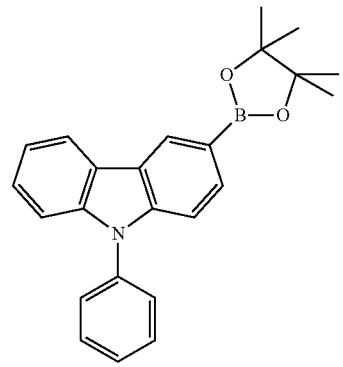

Pd₂(dba)₃, SPhos
KOAc, toluene

A mixture solution of 3-bromo-9-phenyl-9H-carbazole (27.5 g, 72.5 mmol), 4,4,4',4',5,5,5',5'-octamethyl-2,2'-bi(1,3,2-dioxaborolane) (36.8 g, 145 mmol), Pd₂(dba)₃ (0.664 g, 0.725 mmol), SPhos (1.191 g, 2.90 mmol) and potassium acetate (17.80 g, 181 mmol) in dioxane (350 mL) was heated at 110° C. until thin-film chromatography indicated complete conversion. After cooling to room temperature, the reaction mixture was passed through a plug of Centel). Upon evaporation off the solvent, the crude product was purified by column chromatography on silica gel with hexanes/EtOAc (97/3 to 96/4, v/v) as eluent to yield 9-phenyl-3-(4,4,5,5-tetramethyl-1,3,2-dioxaborolan-2-yl)-9H-carbazole (10.4 g, 39%) as a white solid.

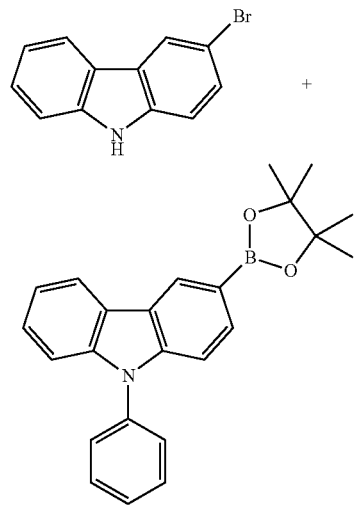 + 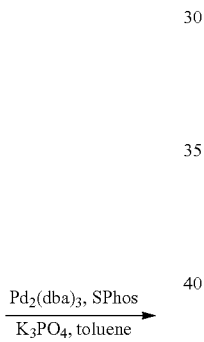

Pd₂(dba)₃, SPhos
K₃PO₄, toluene

-continued

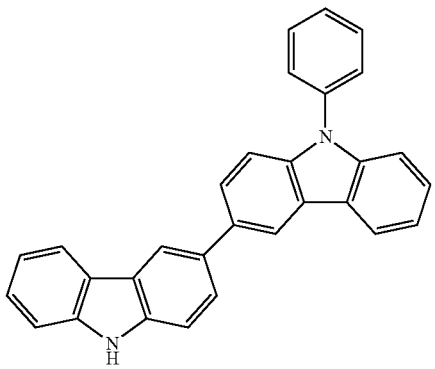

A mixture solution of 3-bromo-9H-carbazole (6.75 g, 27.4 mmol), 9-phenyl-3-(4,4,5,5-tetramethyl-1,3,2-dioxaborolan-2-yl)-9H-carbazole (12.15 g, 32.9 mmol), Pd₂(dba)₃ (0.251 g, 0.274 mmol), SPhos (0.450 g, 1.097 mmol) and K₃PO₄ (25.3 g, 110 mmol) in toluene (500 mL) and water (50 mL) was refluxed under nitrogen for 10 h. After cooling to room temperature, the reaction mixture was extracted with dichloromethane and washed with brine. The combined organic solutions were dried over Na₂SO₄, filtered, and the solvent was evaporated to yield a crude product, which was recrystallized from DCM/hexane (1/1, v/v, 1200 mL) to yield 9H,9'H-3,3'-bicarbazole (6.66 g, 59%) as a yellow solid.

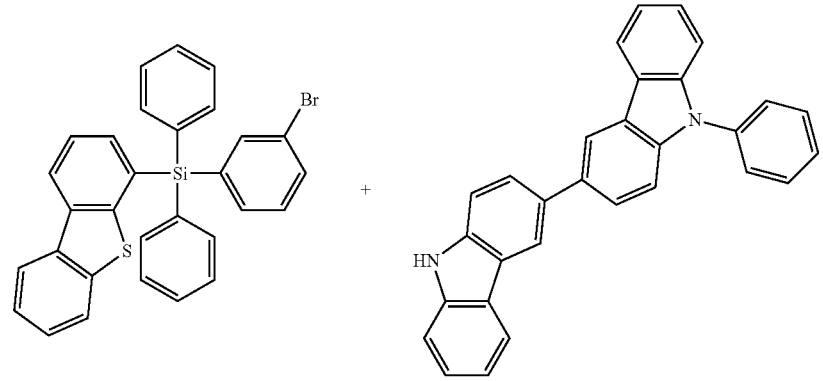

Pd₂(dba)₃, SPhos
tert-BuONa, m-xylene

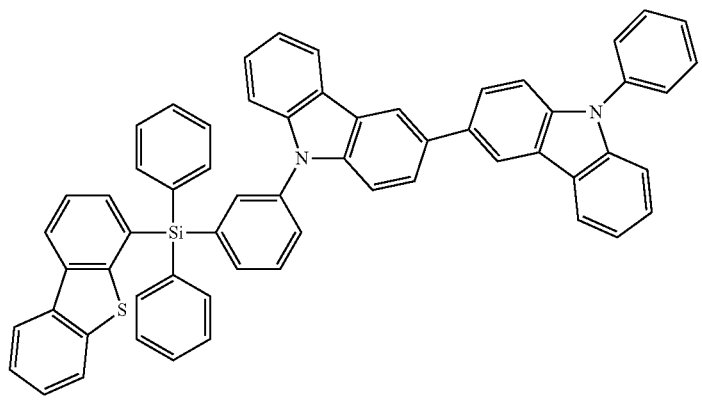

A mixture solution of (3-bromophenyl)(dibenzo[b,d]thiophen-4-yl)diphenylsilane (2.75 g, 5.27 mmol), 9-phenyl-9H,9'H-3,3'-bicarbazole (2.154 g, 5.27 mmol), Pd$_2$(dba)$_3$ (0.097 g, 0.105 mmol), SPhos (0.087 g, 0.211 mmol) and sodium tert-butoxide (1.013 g, 10.55 mmol) in m-xylene (50 ml) was refluxed under nitrogen overnight. After cooling to room temperature, it was passed through a short plug of Celite®, washed with toluene and DCM. The combined solution was evaporated, and the residue was purified by column chromatography on silica gel with hexane/DCM (3/1, v/v) as the eluent to yield Compound 10 (3.7 g, 83%) as a white powder.

Synthesis of Compound 11

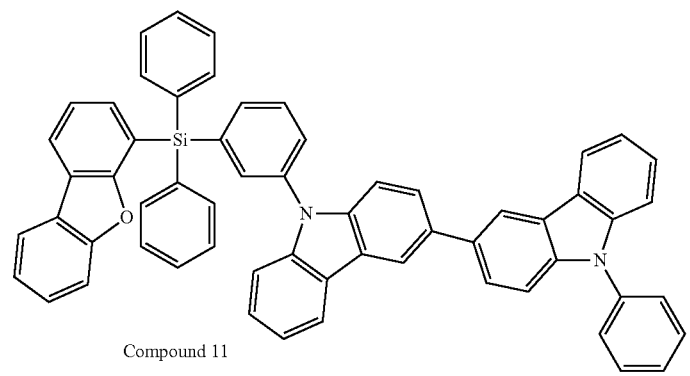

Compound 11

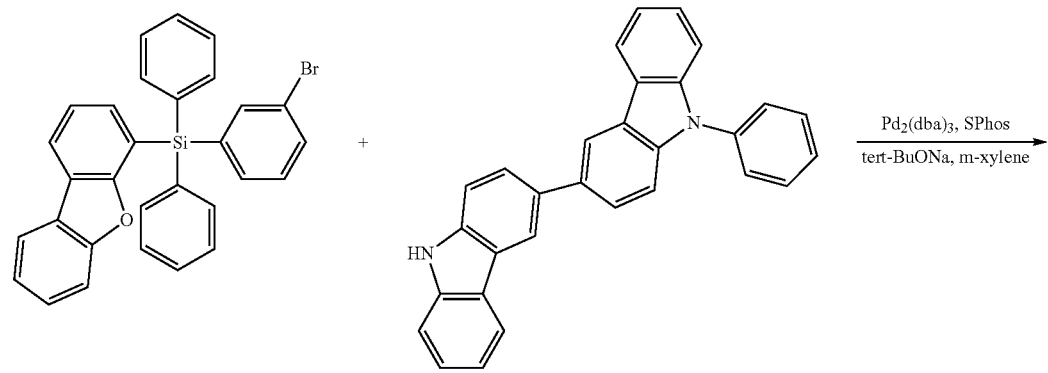

-continued

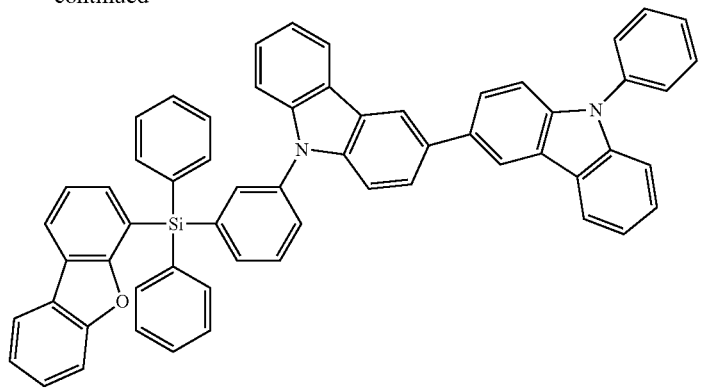

A mixture of (3-bromophenyl)(dibenzo[b,d]furan-4-yl)diphenylsilane (2.75 g, 5.44 mmol), 9-phenyl-9H,9'H-3,3'-bicarbazole (2.222 g, 5.44 mmol), Pd$_2$(dba)$_3$ (0.100 g, 0.109 mmol), SPhos (0.089 g, 0.218 mmol) and sodium tert-butoxide (1.046 g, 10.88 mmol) in m-xylene (50 mL) was refluxed under nitrogen overnight. After cooling to room temperature, it was passed through a short plug of Celite® and washed with toluene and DCM. The combined solution was evaporated, and the residue was purified by column chromatography on silica gel with hexane/DCM (3/1, v/v) as the eluent to yield Compound 11 (3.6 g, 79%) as a white powder.

Comparative Examples

Synthesis of Comparative Compound CC-1

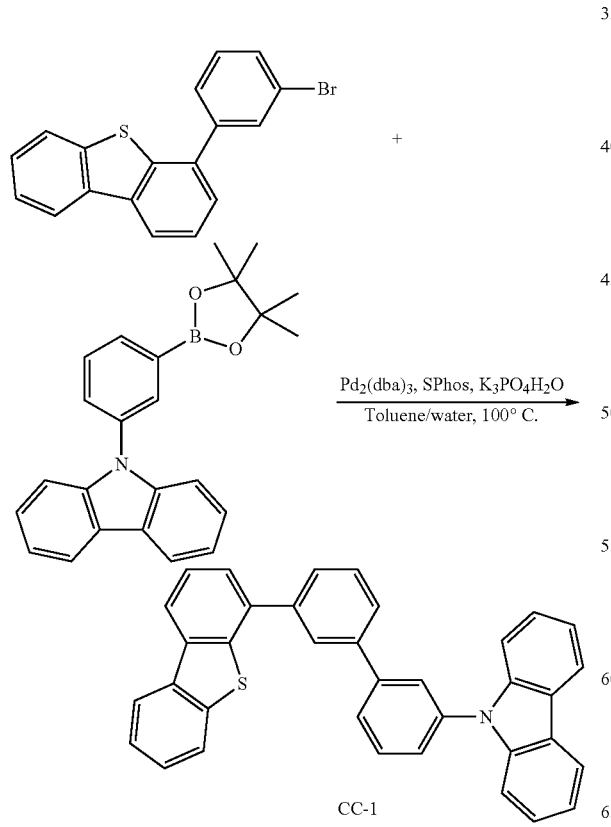

A solution of 4-(3-bromophenyl)dibenzo[b,d]thiophene (7.15 g, 21.08 mmol), 9-(3-(4,4,5,5-tetramethyl-1,3,2-dioxaborolan-2-yl)phenyl)-9H-carbazole (7.78 g, 21.08 mmol), SPhos (0.173 g, 0.422 mmol), Pd$_2$(dba)$_3$ (0.192 g, 0.211 mmol) and potassium phosphate monohydrate (9.71 g, 42.2 mmol) in toluene (200 mL) and water (10 mL) was refluxed under nitrogen overnight. After cooling to room temperature, the organic phase was isolated and evaporated to dryness. The residue was purified by column chromatography on silica gel with hexane/DCM (9/1 to 1/1, v/v) as eluent, recrystallization from heptane, and sublimation under vacuum to yield CC-1 (6.4 g, 61%) as white crystals.

Synthesis of Comparative Compound CC-2

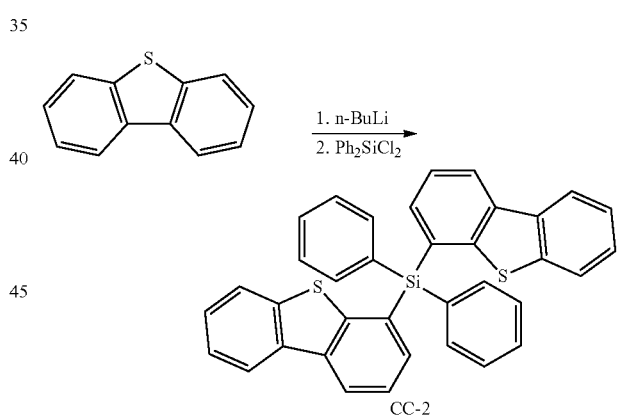

Dibenzo[b,d]thiophene (10 g, 54.3 mmol) was dissolved in THF (500 mL) and the solution cooled to −78° C. n-Butyllithium (40.7 mL, 65.1 mmol, 1.6 M in hexane) was then added dropwise. The mixture was then warmed to room temperature and stirred for 5 h before re-cooling to −78° C. In a separate flask, dichlorodiphenylsilane (4.5 mL, 21.7 mmol) was dissolved in 10 mL of THF and added dropwise to reaction mixture, which was then allowed to warm to room temperature overnight. The reaction mixture was quenched with EtOH (10 mL) and all solvents removed under reduced pressure. To the resulting residue was added DCM (200 mL) and water (200 mL) and the layers separated. The aqueous layer was washed twice more with DCM and combined organics washed with water and brine. Removal of the solvent under reduced pressure gave 14.7 g of an off-white solid. The crude product was chromatographed on silica gel with hexane/

EtOAc (95/5 to 90/10, v/v) as eluent to give Comparative Compound CC-2 (5.4 g, 45%) as a white solid.

Synthesis of Comparative Compound CC-3

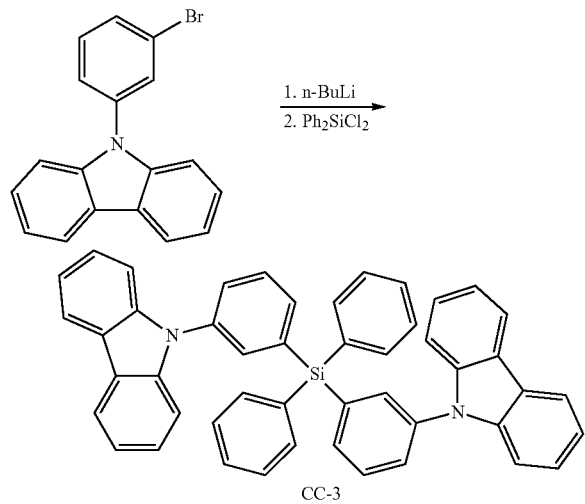

CC-3

Into a solution of 9-(3-bromophenyl)-9H-carbazole (5 g, 15.52 mmol) in THF (50 mL) was added n-butyllithium (9.7 mL, 15.5 mmol, 1.6 M in hexane) dropwise at −78° C., and the mixture was stirred for 2 h at −78° C. In a separate flask, dichlorodiphenylsilane (1.5 mL, 7.1 mmol) was dissolved in 10 mL of THF and added dropwise to reaction mixture, which was then allowed to warm to room temperature overnight. EtOAc (50 mL) and water (50 mL) were added and the layers separated. The aqueous layer was washed twice more with EtOAc and combined organics were washed with water and brine. Upon evaporation of the solvent, the residue was purified by column chromatography on silica gel with hexane/DCM (7/3, v/v) as eluent, recrystallization from hexane, and sublimation twice under vacuum (<$10^{-5}$ Torr) to yield CC-3 (1.7 g, 33%) as white crystals.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound of Formula I comprising:

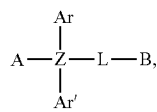

Formula I wherein Ar and Ar' are independently selected from the group consisting of phenyl, biphenyl, naphthyl, dibenzothiophene, and dibenzofuran, which are optionally further substituted;

wherein Z is selected from Si and Ge;

wherein L is a single bond or comprises aryl, amino, or combinations thereof;

wherein L is optionally further substituted;

wherein A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with at least one group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to the group directly bonded to Z; and wherein B contains a group selected from the group consisting of carbazole, azacarbazole, and combinations thereof, which are optionally further substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole or azacarbazole group.

2. The compound of claim 1, wherein A is selected from the group consisting of:

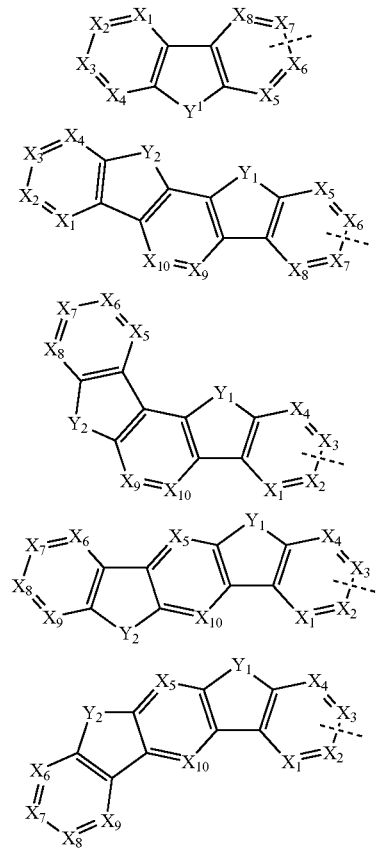

125
-continued
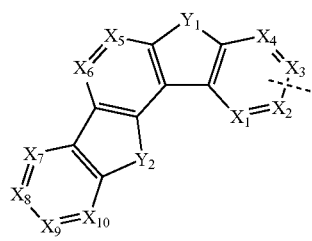
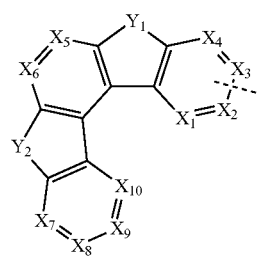
wherein B is selected from the group consisting of:
126
-continued
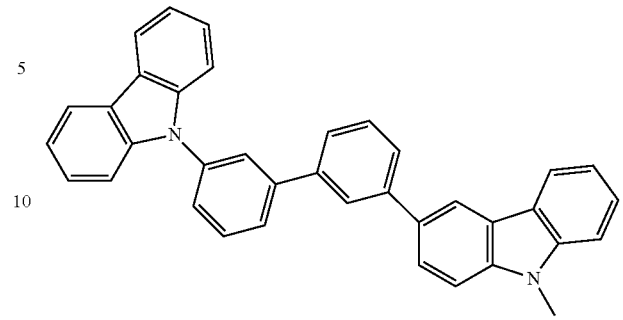
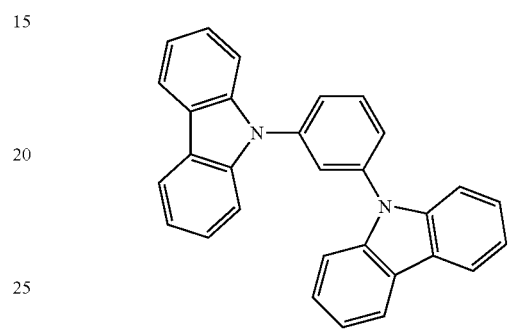
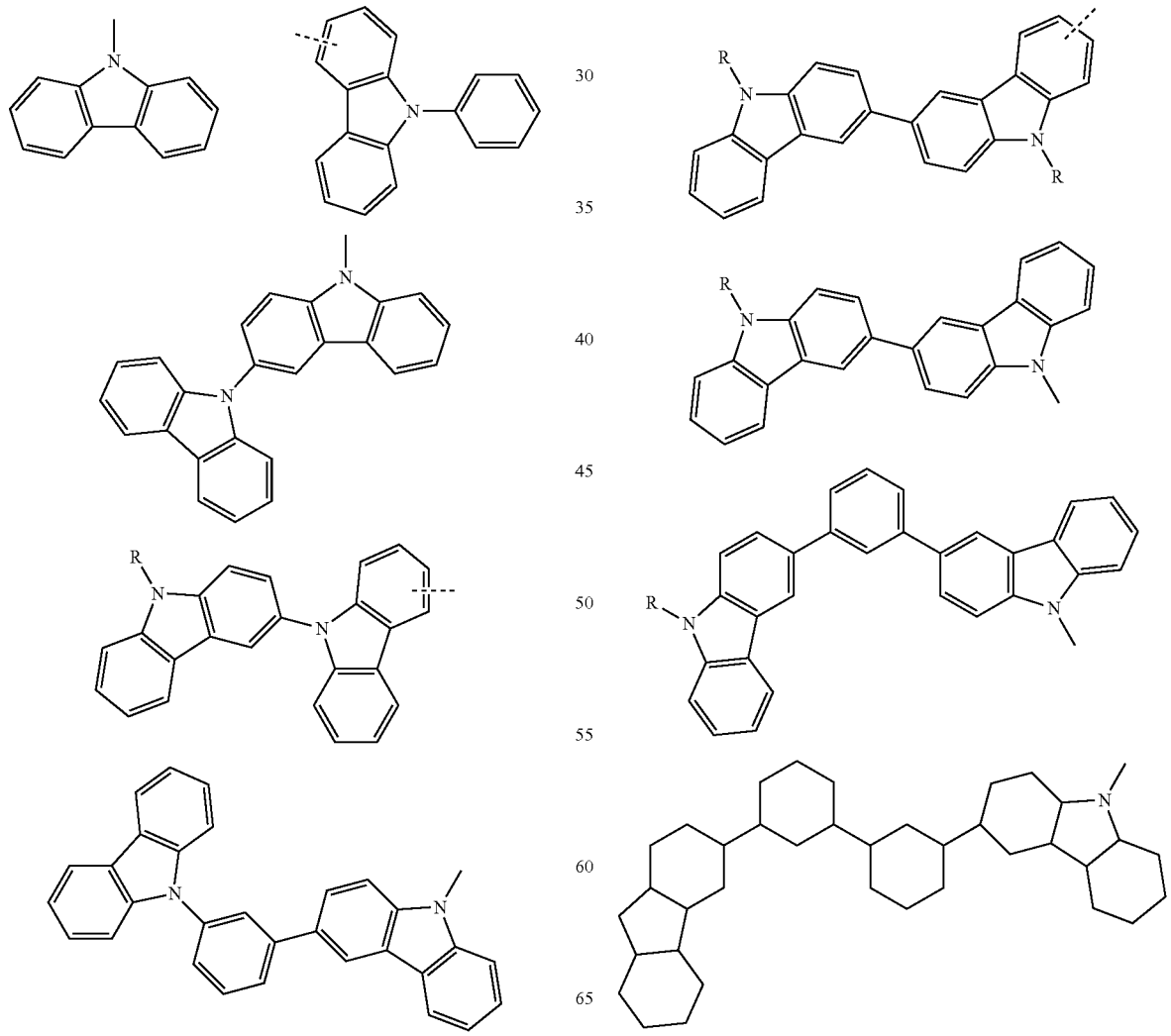

-continued

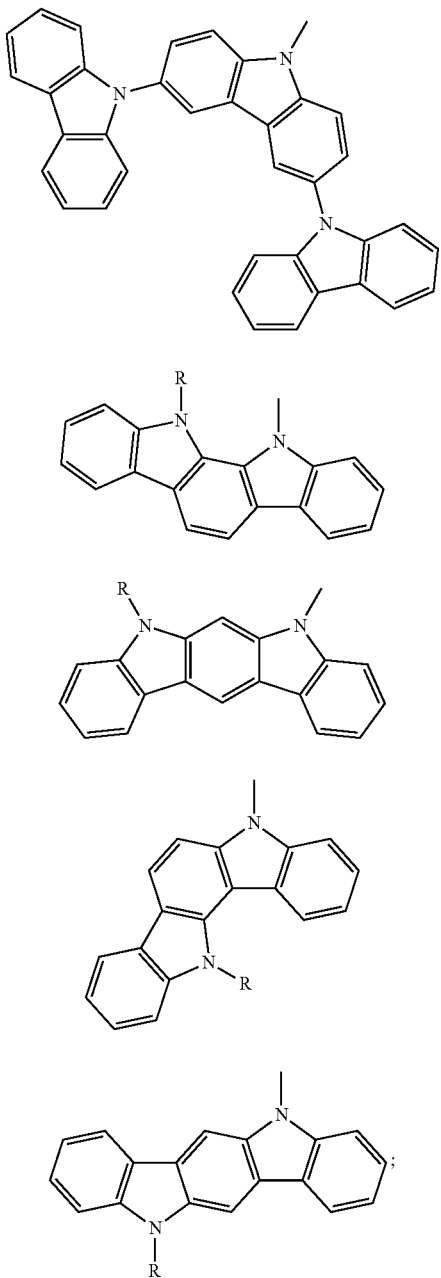

wherein $Y_1$ and $Y_2$ are independently selected from the group consisting of O, S, and Se;

wherein $X_1$ to $X_{10}$ are independently selected from the group consisting of CR' and N, and wherein each benzo ring contains at most one N;

wherein R' is selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof; and wherein R is selected from the group consisting of hydrogen, deuterium, halide, alkyl, cycloalkyl, heteroalkyl, arylalkyl, alkoxy, aryl, heteroaryl, aryloxy, amino, and combinations thereof.

3. The compound of claim 1, wherein L is selected from the group consisting of:

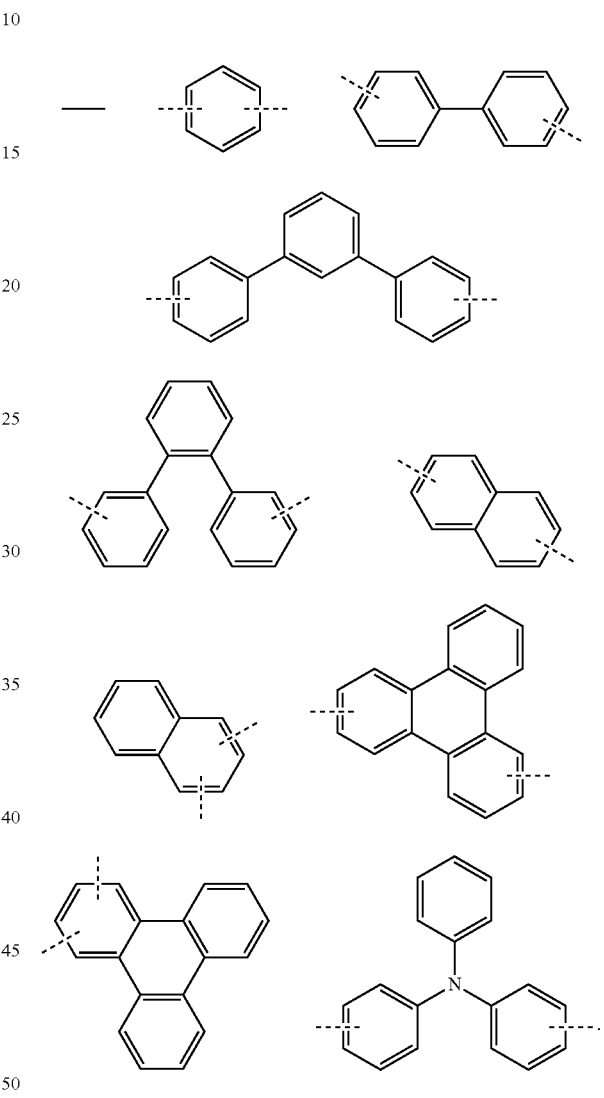

4. The compound of claim 1, wherein L is a single bond.

5. The compound of claim 1, wherein L contains at least one phenyl bonded directly to Z.

6. The compound of claim 1, wherein Ar and Ar' are phenyl.

7. The compound of claim 1, wherein Ar, Ar' are independently substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

8. The compound of claim 1, wherein the compound is selected from the group consisting of Compound 1
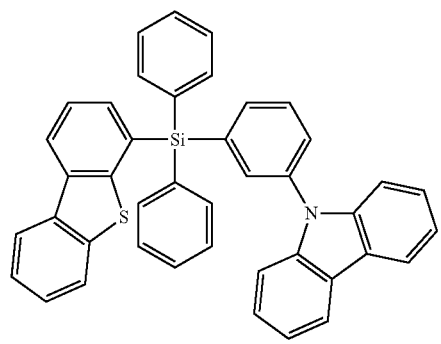
Compound 2
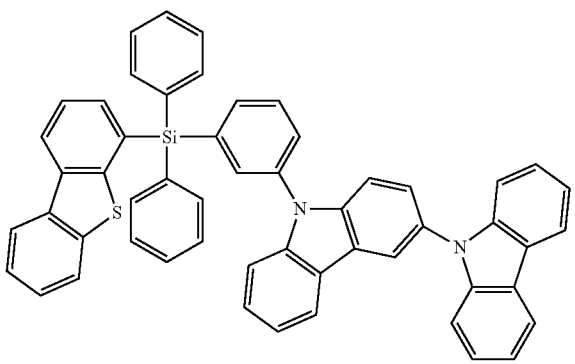
Compound 3
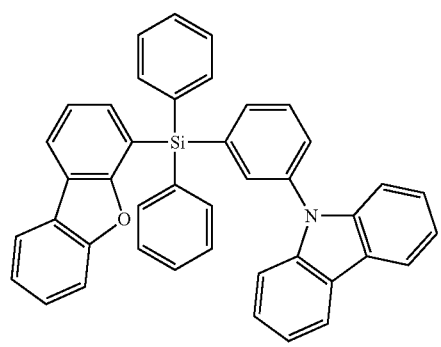
Compound 4
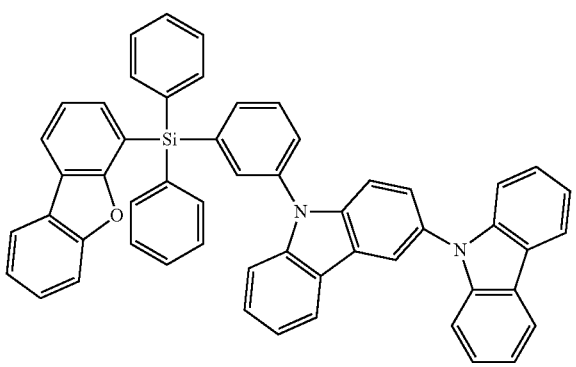
Compound 5
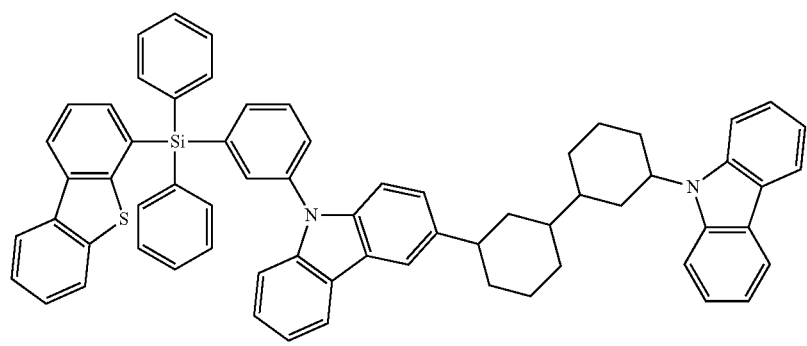
Compound 6
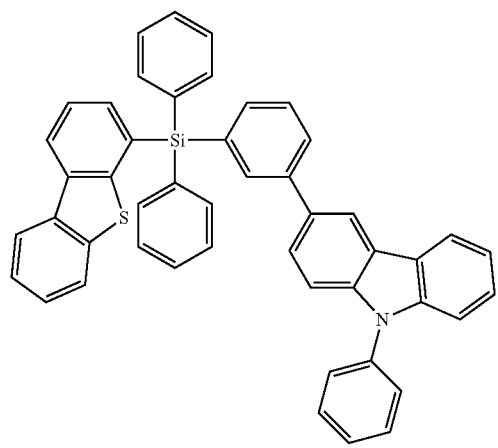
Compound 7
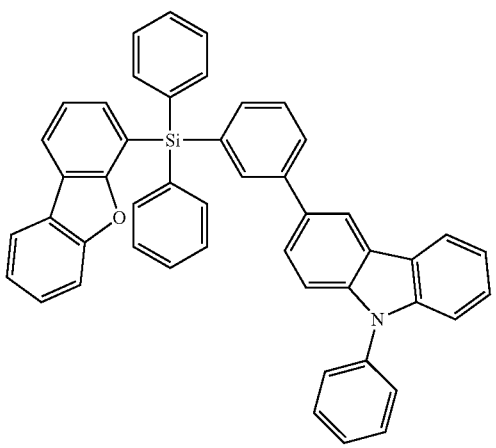

-continued

Compound 6

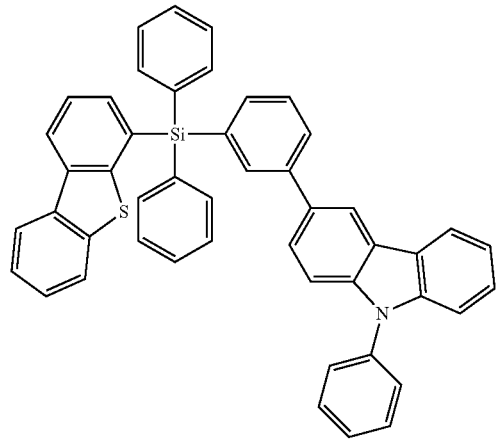

Compound 7

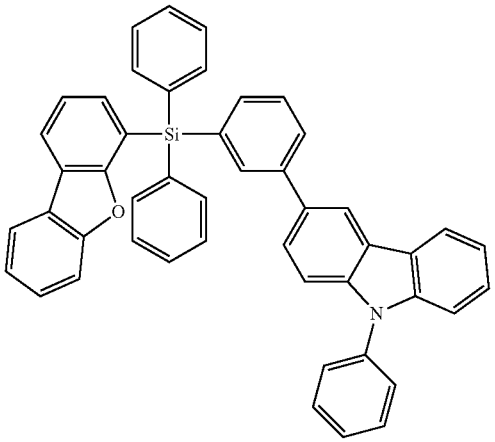

Compound 8

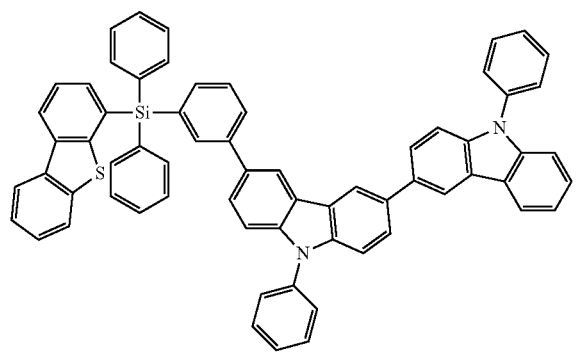

Compound 9

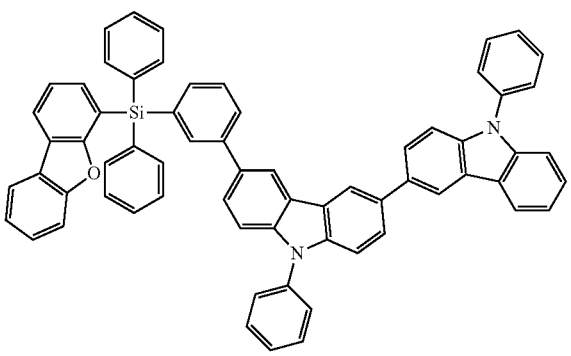

Compound 10

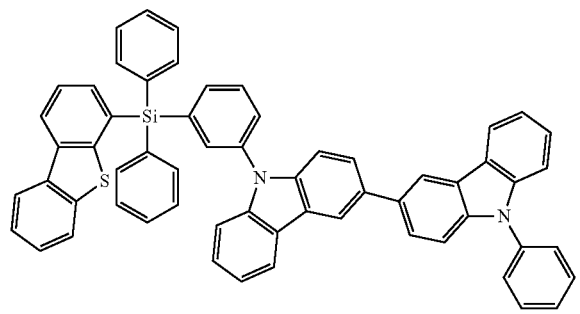

Compound 11

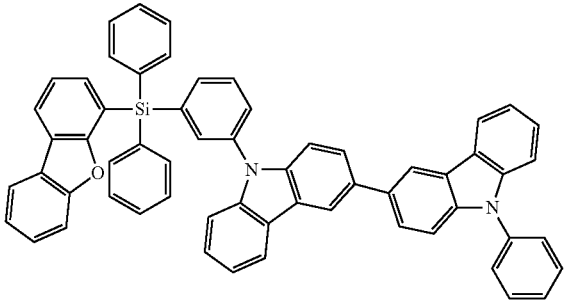

9. A first device comprising an organic light-emitting device, further comprising:
an anode;
a cathode; and
an organic layer, disposed between the anode and the cathode, comprising a compound having the formula:

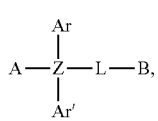

Formula I wherein Ar and Ar' are independently selected from the group consisting of phenyl, biphenyl, naphthyl, dibenzothiophene, and dibenzofuran, which are optionally further substituted;

wherein Z is selected from Si and Ge;
wherein L is a single bond or comprises aryl, amino, or combinations thereof;
wherein L is optionally further substituted;
wherein A is a group directly bonded to Z and is selected from the group consisting of dibenzofuran, dibenzothiophene, azadibenzofuran, azadibenzothiophene, dibenzoselenophene, azadibenzoselenophene, and combinations thereof, which are optionally further substituted with at least one group selected from the group consisting of hydrogen, deuterium, halide, alkyl, cycloalkyl, heteroalkyl, arylalkyl, aryl, aryloxy, arylthio, arylseleno, pyridine, triazine, imidazole, benzimidazole, nitrile, isonitrile, and combinations thereof, and wherein the substitution is optionally fused to the group directly bonded to Z; and
wherein B contains a group selected from the group consisting of carbazole, azacarbazole, and combinations thereof, which are optionally further substituted with at least one group selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein the substitution is optionally fused to the carbazole or azacarbazole group.

10. The first device of claim 9, wherein the organic layer is an emissive layer and the compound of Formula I is a host.

11. The first device of claim 9, wherein the organic layer further comprises an emissive dopant.

12. The first device of claim 11, wherein the emissive dopant is a transition metal complex having at least one ligand selected from the group consisting of:

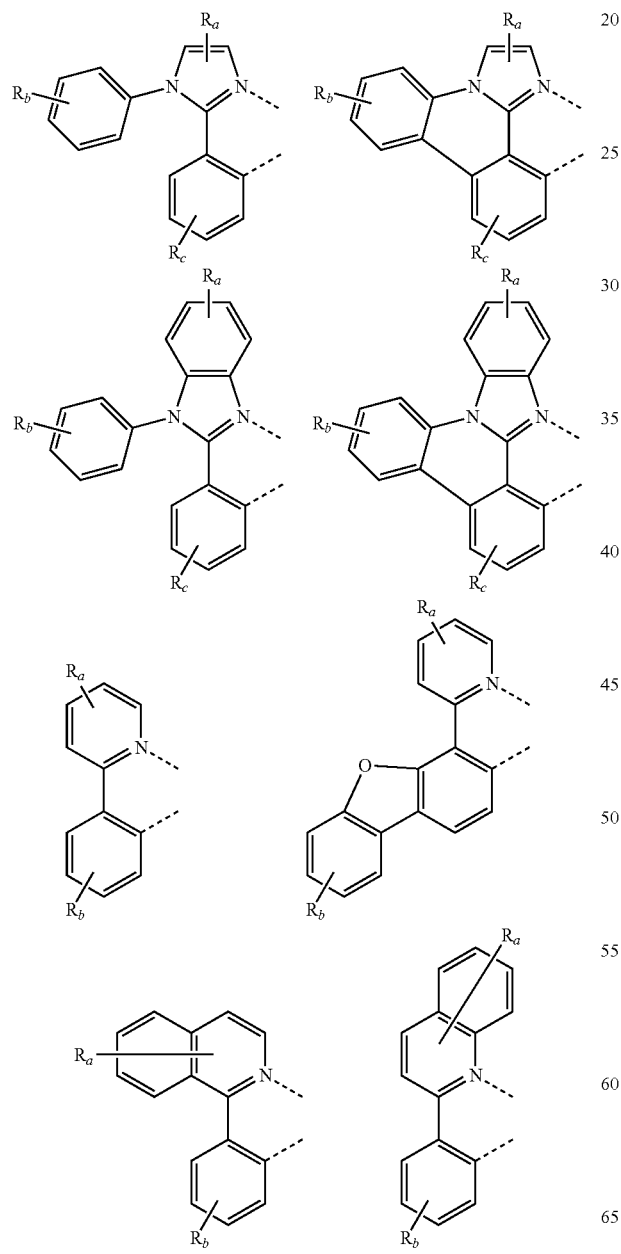
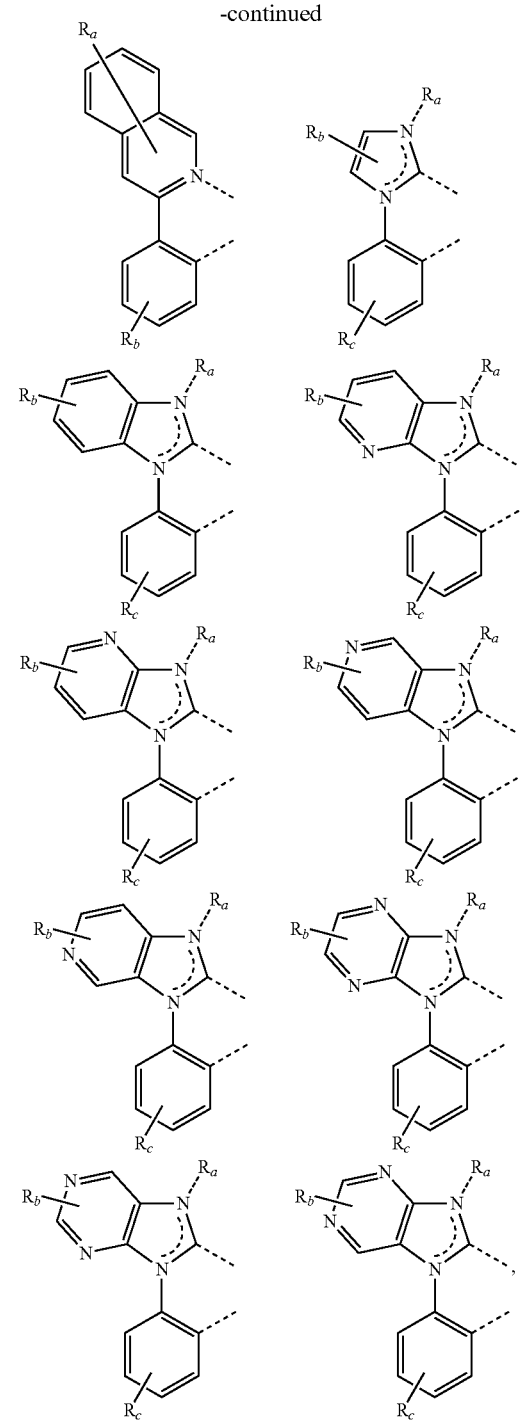

wherein $R_a$, $R_b$, and $R_c$ may represent mono, di, tri or tetra substitutions;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and are optionally joined to form a fused ring.

13. The first device of claim 9, wherein the emissive dopant having the formula

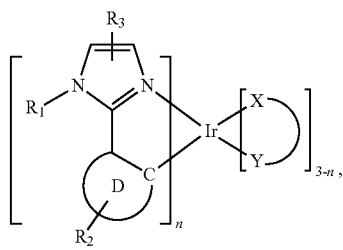

wherein D is a 5- or 6-membered carbocyclic or heterocyclic ring;

wherein $R_1$, $R_2$, and $R_3$ independently represent mono, di, tri or tetra substitution;

wherein each of $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R_1$ can be optionally linked to ring D;

wherein n is 1, 2, or 3; and wherein X—Y is another ligand.

14. The first device of claim 9, wherein the device further comprises a second organic layer that is a non-emissive layer and the compound having Formula I is a material in the second organic layer.

15. The first device of claim 14, wherein the second organic layer is a blocking layer and the compound having Formula I is a blocking material in the second organic layer.

16. The first device of claim 9, wherein the second organic layer is an electron transporting layer and the compound having the Formula I is an electron transporting material in the second organic layer.

17. The first device of claim 9, wherein the first device is a consumer product.

18. The first device of claim 9, wherein the first device is an organic light-emitting device.

* * * * *